US011539001B2

(12) United States Patent
Runge et al.

(10) Patent No.: US 11,539,001 B2
(45) Date of Patent: Dec. 27, 2022

(54) COMPOUND, ORGANIC ELECTRONIC DEVICE COMPRISING THE SAME, AND DISPLAY DEVICE AND LIGHTING DEVICE COMPRISING THE SAME

(71) Applicant: Novaled GmbH, Dresden (DE)

(72) Inventors: Steffen Runge, Dresden (DE);
Benjamin Schulze, Dresden (DE);
Omrane Fadhel, Dresden (DE);
Gregor Schwartz, Dresden (DE);
Volodymyr Senkovskyy, Dresden (DE);
Chao Wu, Dresden (DE)

(73) Assignee: Novaled GmbH, Dresden (DE)

( * ) Notice: Subject to any disclaimer, the term of this patent is extended or adjusted under 35 U.S.C. 154(b) by 413 days.

(21) Appl. No.: 16/683,508

(22) Filed: Nov. 14, 2019

(65) Prior Publication Data

US 2020/0161565 A1 May 21, 2020

(30) Foreign Application Priority Data

Nov. 16, 2018 (EP) .................................. 18206770

(51) Int. Cl.
| | | |
|---|---|---|
| *H01L 51/00* | (2006.01) | |
| *C07D 221/18* | (2006.01) | |
| *C07D 401/10* | (2006.01) | |
| *C07D 401/14* | (2006.01) | |
| *C09K 11/06* | (2006.01) | |
| *H01L 51/50* | (2006.01) | |

(52) U.S. Cl.
CPC ........ *H01L 51/0072* (2013.01); *C07D 221/18* (2013.01); *C07D 401/10* (2013.01); *C07D 401/14* (2013.01); *C09K 11/06* (2013.01); *H01L 51/0061* (2013.01); *C09K 2211/1018* (2013.01); *H01L 51/0052* (2013.01); *H01L 51/5012* (2013.01); *H01L 51/5016* (2013.01); *H01L 51/5072* (2013.01); *H01L 51/5096* (2013.01); *H01L 2251/552* (2013.01)

(58) Field of Classification Search
CPC ............ C09K 11/06; C09K 2211/1018; C09K 2211/1007; C09K 2211/1029; C07D 221/18; C07D 401/10; C07D 401/14; C07D 403/10; C07D 401/04; H01L 51/0072; H01L 51/0061; H01L 51/0052; H01L 51/5012; H01L 51/5016; H01L 51/5072; H01L 51/5096; H01L 2251/552
USPC ......................................................... 428/690
See application file for complete search history.

(56) References Cited

U.S. PATENT DOCUMENTS

| | | | | |
|---|---|---|---|---|
| 7,183,010 | B2 * | 2/2007 | Jarikov | ............... H01L 51/0054 313/506 |
| 8,415,473 | B2 * | 4/2013 | Yam | .................... H01L 51/0091 428/917 |
| 10,897,014 | B2 * | 1/2021 | Sim | ....................... C07D 221/18 |
| 11,001,752 | B2 * | 5/2021 | Cha | .......................... C09K 11/06 |
| 11,011,708 | B2 * | 5/2021 | Frey | ..................... C07D 251/24 |
| 11,011,723 | B2 * | 5/2021 | Jankus | ................ H01L 51/0045 |
| 2007/0252140 | A1 | 11/2007 | Limmert et al. | |
| 2008/0265216 | A1 | 10/2008 | Hartmann et al. | |
| 2009/0212280 | A1 | 8/2009 | Werner et al. | |
| 2013/0200341 | A1 * | 8/2013 | Fadhel | ................ H01L 51/5028 257/40 |
| 2014/0332790 | A1 * | 11/2014 | Fadhel | ...................... C07F 9/64 257/40 |
| 2015/0280136 | A1 | 10/2015 | Ryu et al. | |
| 2016/0322581 | A1 | 11/2016 | Hwang et al. | |
| 2018/0019410 | A1 | 1/2018 | Sim et al. | |
| 2018/0114940 | A1 * | 4/2018 | Pavicic | ................ C07D 495/04 |
| 2019/0067595 | A1 | 2/2019 | Jang et al. | |
| 2019/0207116 | A1 * | 7/2019 | Runge | ................. H01L 51/0052 |
| 2019/0322642 | A1 * | 10/2019 | Schulze | ............. H01L 51/0054 |
| 2020/0071276 | A1 * | 3/2020 | Cardinali | ................ H01L 51/50 |
| 2021/0091311 | A1 * | 3/2021 | Cardinali | .............. H01L 51/008 |
| 2022/0037595 | A1 * | 2/2022 | Schulze | ............. H01L 51/5076 |
| 2022/0069230 | A1 * | 3/2022 | Schulze | ............. H01L 51/0071 |

FOREIGN PATENT DOCUMENTS

| | | |
|---|---|---|
| CN | 103539737 A | 1/2014 |
| CN | 104672211 A | 6/2015 |
| EP | 1970371 A1 | 9/2008 |
| EP | 3312899 A1 | 4/2018 |
| JP | 201496418 A | 5/2014 |
| WO | 2011/154131 A1 | 12/2011 |
| WO | 2013079217 A1 | 6/2013 |
| WO | 2015/083948 A1 | 11/2015 |
| WO | 2016171358 A1 | 10/2016 |
| WO | 2016180891 A1 | 11/2016 |

OTHER PUBLICATIONS

Translation of CN 104672211, Jun. 3, 2015. (Year: 2015).*
European Office Action for EP Application No. 18206770.2 dated May 11, 2021 (6 pages).

* cited by examiner

*Primary Examiner* — Douglas J Mc Ginty

(74) *Attorney, Agent, or Firm* — Eversheds Sutherland (US) LLP

(57) ABSTRACT

The present invention relates to compounds that include a nitrogen heteroatom, including a compound of the formula (I).
Also provided herein is an organic electronic device comprising the compound and a display device or lighting device comprising the organic electronic device.

14 Claims, 2 Drawing Sheets

COMPOUND, ORGANIC ELECTRONIC DEVICE COMPRISING THE SAME, AND DISPLAY DEVICE AND LIGHTING DEVICE COMPRISING THE SAME

CROSS REFERENCE TO RELATED APPLICATIONS

This application claims priority to European Patent Application No. 18206770.2, filed Nov. 16, 2018, which is incorporated herein by reference.

FIELD OF THE INVENTION

The present invention relates to a compound and an organic electronic device comprising the same. The invention further relates to a display device or a lighting device comprising the organic electronic device.

BACKGROUND ART

Organic light-emitting diodes (OLEDs), which are self-emitting devices, have a wide viewing angle, excellent contrast, quick response, high brightness, excellent driving voltage characteristics, and color reproduction. A typical OLED includes an anode, a hole transport layer (HTL), an emission layer (EML), an electron transport layer (ETL), and a cathode, which are sequentially stacked on a substrate. In this regard, the HTL, the EML, and the ETL are thin films formed essentially by organic and/or organometallic compounds.

When a voltage is applied to the anode and the cathode, holes injected from the anode electrode move to the EML, via the HTL, and electrons injected from the cathode electrode move to the EML, via the ETL. The holes and electrons mainly recombine in the EML to generate excitons. When the excitons drop from an excited state to a ground state, light is emitted. The injection and flow of holes and electrons should be balanced, so that an OLED having the above-described structure has excellent efficiency.

A variety of organic light-emitting diodes and devices comprising the same is known in the art. Furthermore, the use of respective OLEDs comprising benzoacridine compounds in one or more of the layers thereof is known in the art.

Nevertheless, there is still a need to improve the electronic properties of a respective compound for use in organic electronic devices, in particular to provide a compound suitable to improve the performance of OLEDs, in particular with respect to operating lifetime at comparable voltage.

It is, therefore, the object of the present invention to provide novel compounds for use in organic electronic devices overcoming drawbacks of the prior art, in particular compounds suitable to improve the performance of top emission and bottom emission OLEDs with respect to operating lifetime.

The above object is achieved by a compound of the Formula (I)

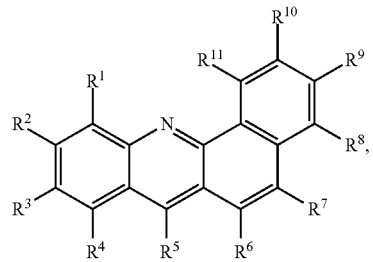

wherein all of $R^1$ to $R^{11}$, except one, are independently selected from the group consisting of H, D, F, substituted or unsubstituted $C_1$ to $C_{18}$ alkyl, substituted or unsubstituted $C_6$ to $C_{42}$ aryl, substituted or unsubstituted $C_3$ to $C_{42}$ heteroaryl; and adjacent groups R1 to R11 may be linked to each other to form a fused ring, wherein the one of $R^1$ to $R^{11}$ not selected from the above groups is a group G, wherein the group G comprises one atom A having an electron pair in a p-orbital thereof;

the group G comprises two 6-membered aryl rings which are attached to the atom A, wherein each of the two 6-membered aryl rings is attached to the atom A via a single bond respectively; and wherein the two 6-membered aryl rings attached to the atom A may be connected with each other via a single bond;

the group G comprises 12 to 66 carbon atoms in total;

the group G is attached to the benzoacridine part of the compound of formula (I) via a single bond or via a $C_6$ to $C_{18}$ arylene group, wherein the $C_6$ to $C_{18}$ arylene group is part of the group G; and the group G is unsubstituted or substituted with one or more substituents independently selected from the group consisting of D, F, C, to $C_{18}$ alkyl, $C_6$ to $C_{42}$ aryl, $C_6$ to $C_{42}$ heteroaryl, $(R^{12})_2P=O$, CN or G', wherein the group G' is defined likewise the group G with the exception that the group G' is not attached to the benzoacridine part of the compound of formula (I) but to the group G via a single bond or via a $C_6$ to $C_{18}$ arylene group, wherein the $C_6$ to $C_{18}$ arylene group is part of the group G' provided that in case that the group G is attached to the benzoacridine part of the compound of formula (I) via the $C_6$ to $C_{18}$ arylene group, substituents which may be attached to the $C_6$ to $C_{18}$ arylene group are only selected from the group consisting of C, to $C_{18}$ alkyl, $C_6$ to $C_{42}$ aryl, $(R^{12})_2P=O$ and CN;

wherein in case that at least one of $R^1$ to $R^{11}$, which is not the group G, is substituted, the respective substituent or substituents are independently selected from the group consisting of D, F, $C_1$ to $C_{18}$ alkyl, $C_6$ to $C_{36}$ aryl, $C_6$ to $C_{42}$ heteroaryl, $(R^{12})_2P=O$, CN; and wherein $R^{12}$ are independently selected from the group consisting of $C_1$ to $C_{18}$ alkyl and $C_6$ to $C_{24}$ aryl.

The present inventors surprisingly found that the above compounds when used in certain layers of an organic electronic device, such as in an OLED, are suitable to improve the performance thereof, in particular with respect to operating lifetime.

The p-orbital is a non-hybridized orbital.

In case that the group G attached to the benzoacridine part of the compound of Formula (I) is substituted with a further group G', it may be provided that this further group G'—not directly attached to the benzoacridine moiety—does not comprise a further group G' as a substituent thereof.

According to the invention, it is provided that the group G and the group G' is—with respect to the atom A, the two 6-membered aryl rings attached thereto via a single bond and further groups attached to the atom A—substantially planar.

The two 6-membered aryl rings may comprise ring atoms selected from carbon and nitrogen. In an embodiment the ring atoms of the two 6-membered aryl rings are carbon.

The group G may comprise the following structural element

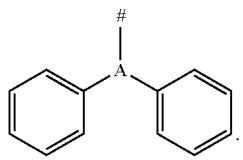

The group G may be attached to the benzoacridine part of the compound of formula (I) at the position indicated by "#".

In the group G, in particular in the structural element above, the two 6-membered aryl rings may be linked with each other via a single bond.

According to the invention, it may be provided that two of the groups $R_1$ to $R_{11}$ which are adjacent to each other (such as, for example, the groups $R^1$ and $R^2$) form together a fused ring. A fused ring in this regard is a second ring that forms, together with the ring to which the two adjacent R″ groups are bound to, a system of fused rings. In this way, the two carbon atoms to which the two R″ groups are bound to are shared by the two adjacent rings fused to each other. Referring to the example, where $R^1$ and $R^2$ form a fused ring the resulting structure may be as follows, wherein ring X is fused to the adjacent ring Y sharing two carbon atoms:

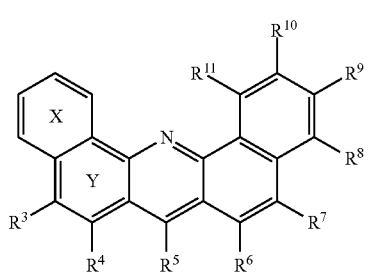

However, it has to be noted that the above embodiment in which $R^1$ and $R^2$ form together a 6-membered aromatic ring (which is the fused ring) is only of exemplary nature and that a formation of other fused rings (for example 5- or 7-membered rings, non-aromatic rings etc.) is included. Nevertheless, it is preferred that the fused ring formed by two adjacent R″ groups is a 6-membered aromatic ring as depicted above.

With respect to the inventive compound, it is provided that exactly one of the groups $R^1$ to $R^{11}$ is the group G, as defined herein. All of the other groups $R^1$ to $R^{11}$ are selected differently from the group referred to above.

The group G comprises one atom A having an electron pair in a p-orbital thereof. The fact that the atom A has an electron pair in a p-orbital thereof results in a chemical structure which is with respect to the atom A and the moieties directly attached thereto substantially planar meaning that the three bonds of A to #, A to First aryl and A to second aryl lie in the same molecular plane in the frame of only few degrees (°) deviation. The deviation may be 10°, alternatively 5°, alternatively <1°.

This shall be exemplified by referring to the following structure:

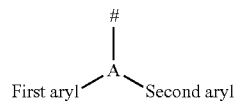

In the above exemplary structure the atom A is—as it is required according to the present invention—directly connected to two 6-membered aryl rings (labeled as "first aryl" and "second aryl" above). In the above case, wherein the atom A is a trivalent atom, such as a nitrogen atom N, the angle between the bond connecting the first aryl group to the atom A and the bond connecting the second aryl bond to the group A is about 120°, such as from 110° to 120°, alternatively 115° to 120°, alternatively 119° to 120°. The same is true with respect to the bond # to the atom A and the respective bonds of A to the first, respective the second, aryl group.

The two 6-membered aryl rings attached to the atom A may or may not be connected to each other via a single bond. In the first case (not connected) the respective structure may be as depicted above.

In case that the two 6-membered aryl rings are connected to each other via a single bond, the group G or G' may comprise the following structure:

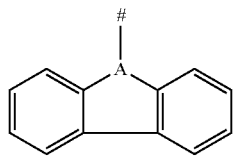

The group G may be attached to the benzoacridine part

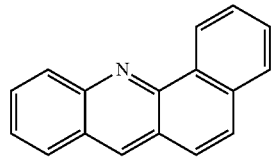 [SMILES: c1ccc2nc3c(ccc4ccccc43)cc2c1]

of the compound of formula (I) via a single bond or via a $C_6$ to $C_{18}$ arylene group at the bond position "#". The $C_6$ to $C_{18}$ arylene group (if present) is part of the group G. That is, in case that the group G is substituted, the substituents attached to the group G may be attached to the $C_6$ to $C_{18}$ arylene part thereof connecting the group G to the benzoacridine part of the compound of Formula (I).

It is provided that the group G comprises only one atom A. However, in a case that the group G is substituted with a further group G', as defined herein, it may be provided that the compound of general formula (I) (but not the group G) comprises a further atom A. The group G' cannot be attached to the $C_6$ to $C_{18}$ arylene group being part of the group G and connecting the same to the benzoacridine part of the compound of formula (I).

In the compound of Formula (I), the group G may comprise 1 to 5 heteroatoms selected from the group consisting of N, S and O. In this way, the ability of the compound of Formula (I) to improve operating lifetime of an organic electronic device comprising the same is further improved.

In the compound of Formula (I), the atom A may be selected from the group consisting of N, S and O. In this way, the ability of the compound of Formula (I) to improve operating lifetime of an organic electronic device comprising the same is further improved.

In the compound of Formula (I), the atom A may be N. In this way, the ability of the compound of Formula (I) to improve operating lifetime of an organic electronic device comprising the same is further improved.

In the compound of Formula (I), the group G may comprise the atom A and the two 6-membered aryl rings attached thereto in the form of a diarylamino group or in the form of a carbazol group. In this way, the ability of the compound of Formula (I) to improve operating lifetime of an organic electronic device comprising the same is further improved.

In the compound of Formula (I), the total number of aromatic rings comprised in the compound of formula (I) may be from 6 to 21. In this way, the ability of the compound of Formula (I) to improve operating lifetime of an organic electronic device comprising the same is further improved.

In the compound of Formula (I), $R^1$ and $R^2$; or $R^2$ and $R^3$; or $R^3$ and $R^4$; may form together an aryl ring. In this regard, only one of the above couples of adjacent groups $R''$ forms a fused ring. The fused ring formed this way is the fused ring referred to above. In this way, the ability of the compound of Formula (I) to improve operating lifetime of an organic electronic device comprising the same is further improved.

In an embodiment $R^1$ and $R^2$; or $R^3$ and $R^4$ may form a fused ring. Preferably, $R^1$ and $R^2$ may form a fused ring.

In the compound of Formula (I), the fused ring formed by $R^1$ and $R^2$; or $R^2$ and $R^3$; or $R^3$ and $R^4$; may be a $C_6$-aryl ring. In this way, the ability of the compound of Formula (I) to improve operating lifetime of an organic electronic device comprising the same is further improved.

In the compound of Formula (I), the group G may be attached to the benzoacridine part of the compound of Formula (I) via an unsubstituted $C_6$ to $C_{18}$ arylene group. In this regard, the unsubstituted $C_6$ to $C_{18}$ arylene group by which the group G is attached to the benzoacridine part may be phenylene. In this way, the ability of the compound of Formula (I) to improve operating lifetime of an organic electronic device comprising the same is further improved.

In the compound of general formula (I), $R^5$ or $R^{10}$ may be the group G. In other words, it is preferred that the group G is attached to the benzoacridine part of the compound of the Formula (I) at the $R^5$ or the $R^{10}$ position. In this way, the ability of compound of general formula (I) to improve operating lifetime of an organic electronic device comprising the same is further improved.

In a very preferred embodiment, the compound of formula (I) is one selected from the following compounds

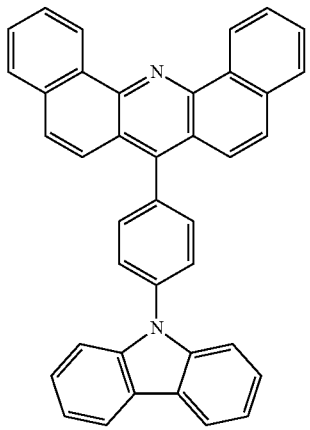

1

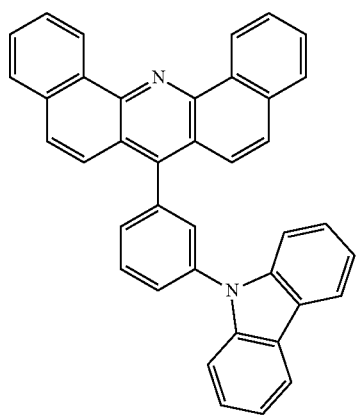

2

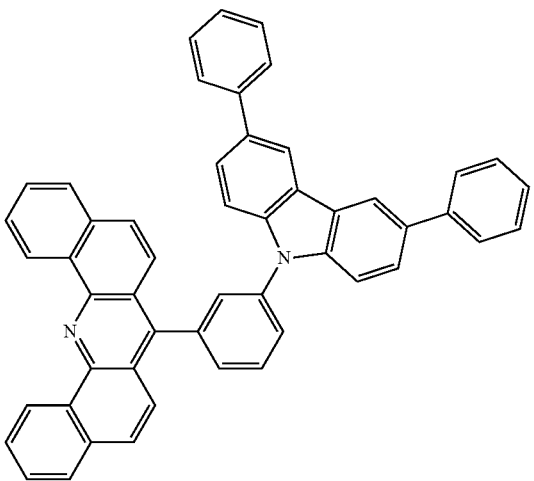

3

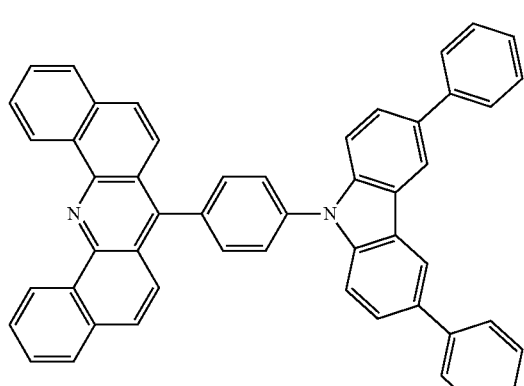
4
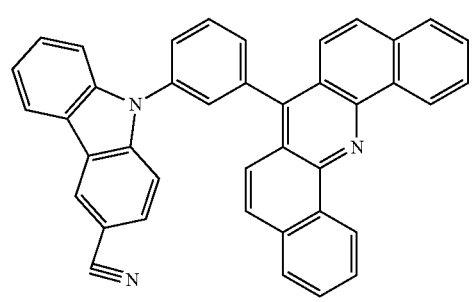
5
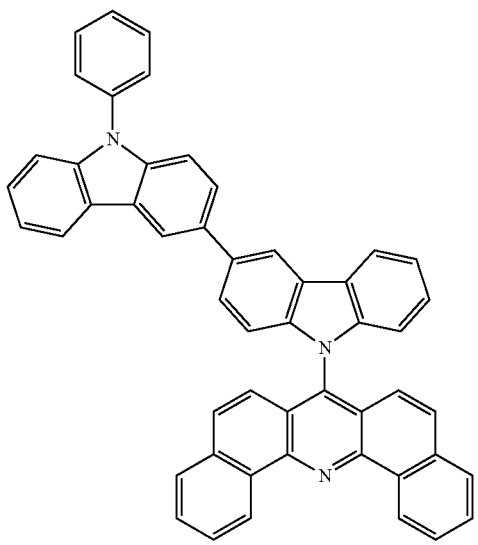
6
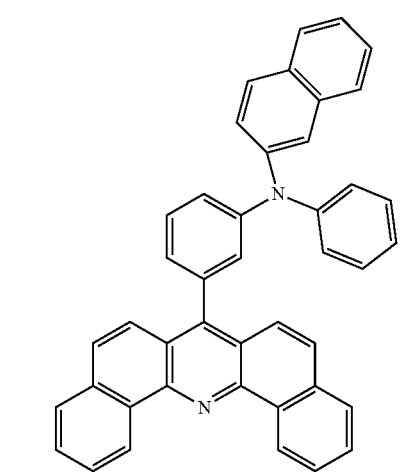
7
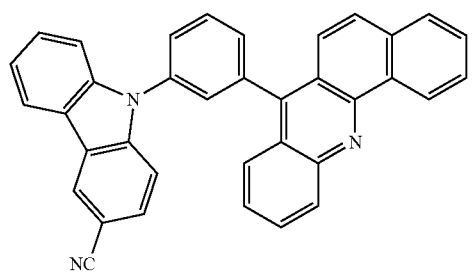
8
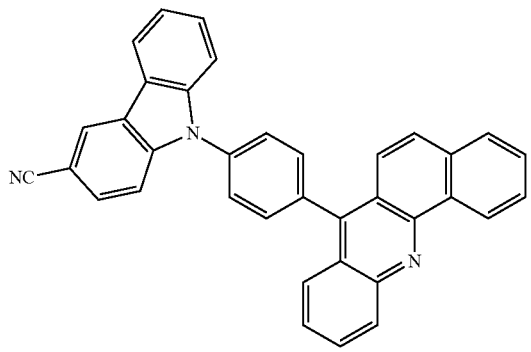
9
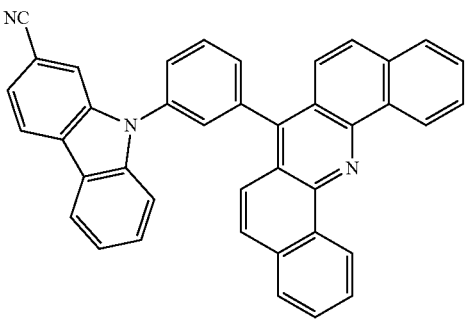
10

11
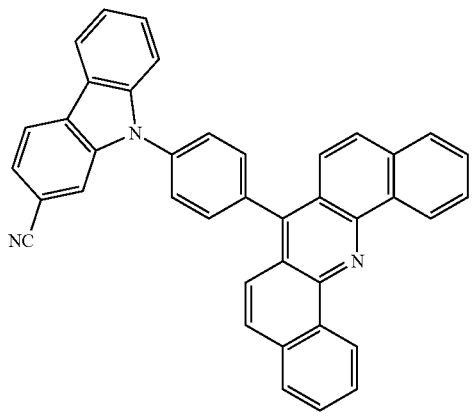
12
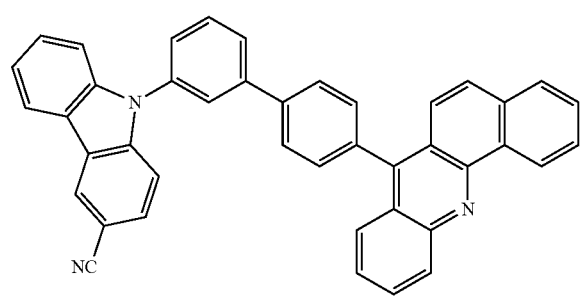
13
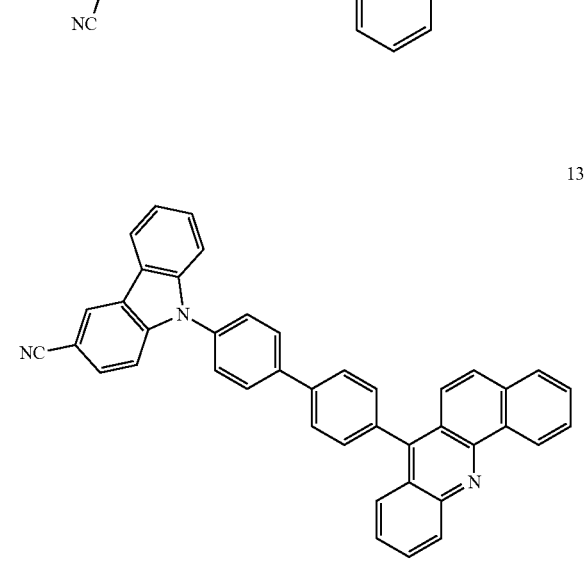
14
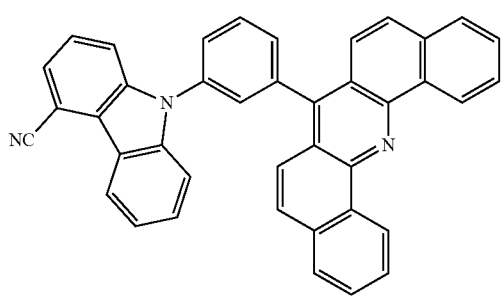
15
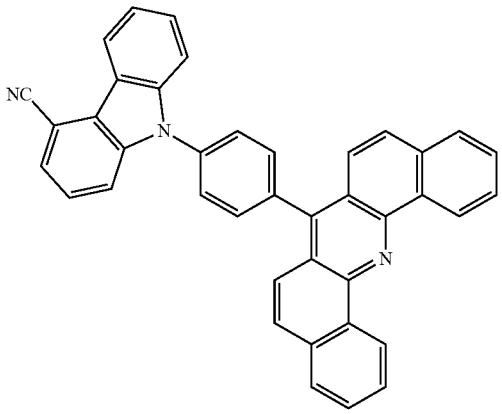
16
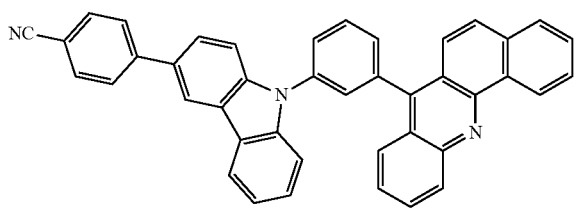
17
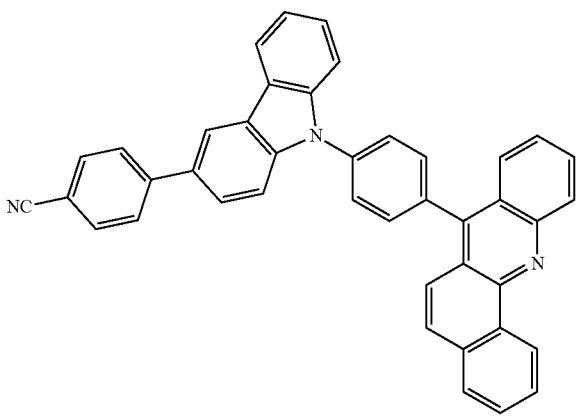
18
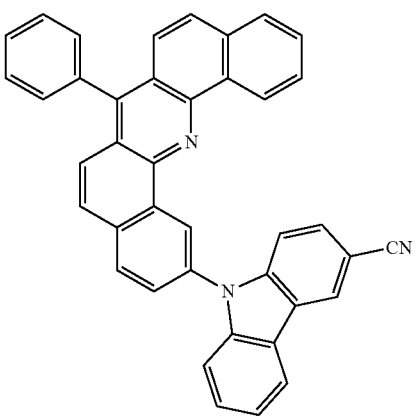

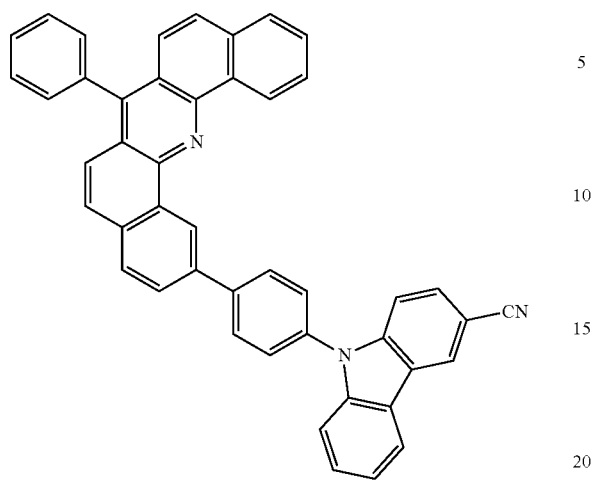
19
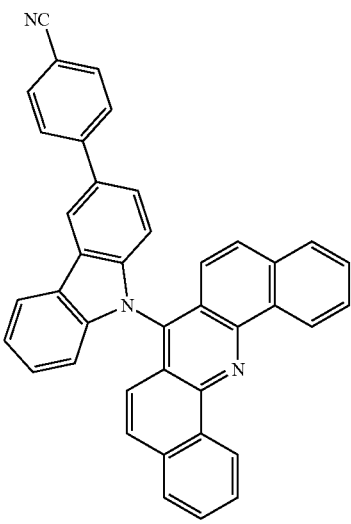
22
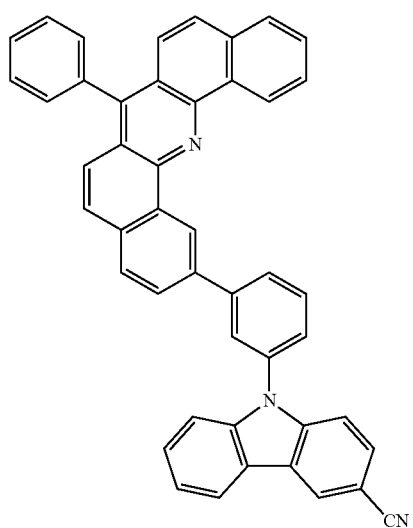
20
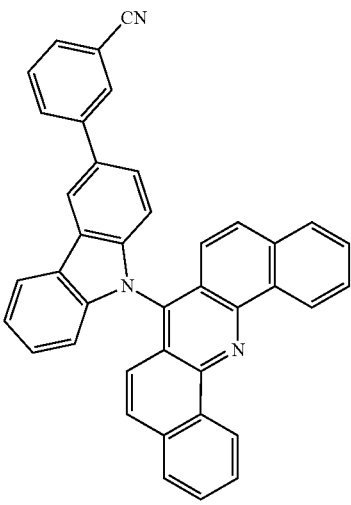
23
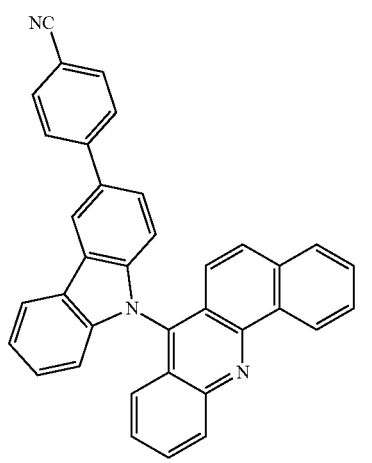
21
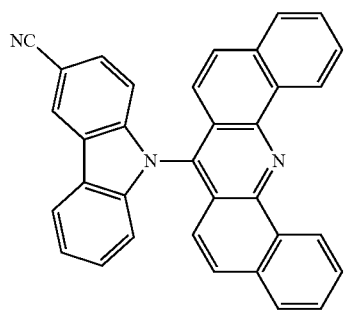
24

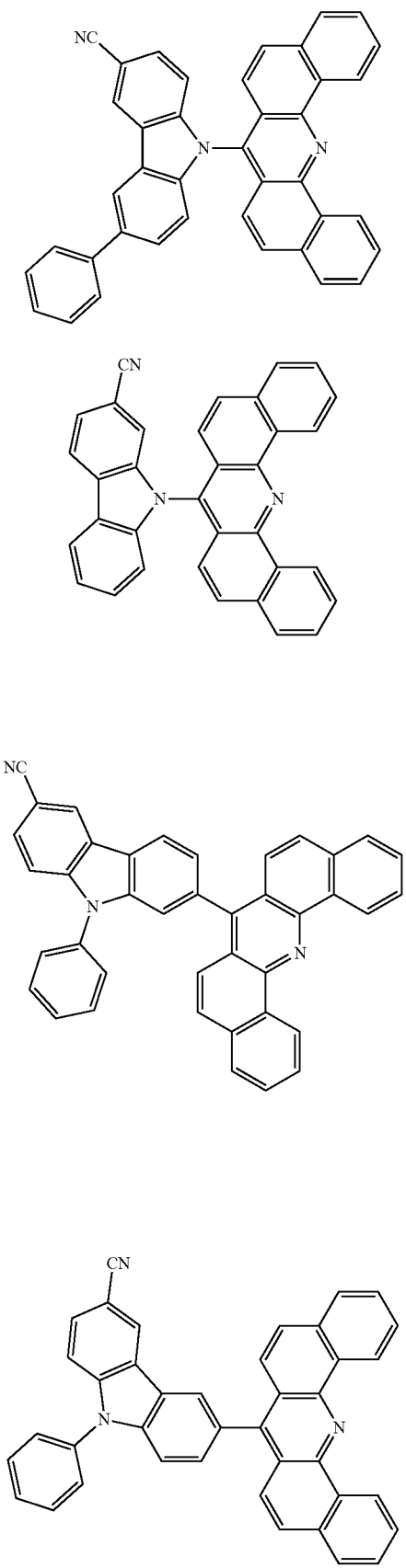

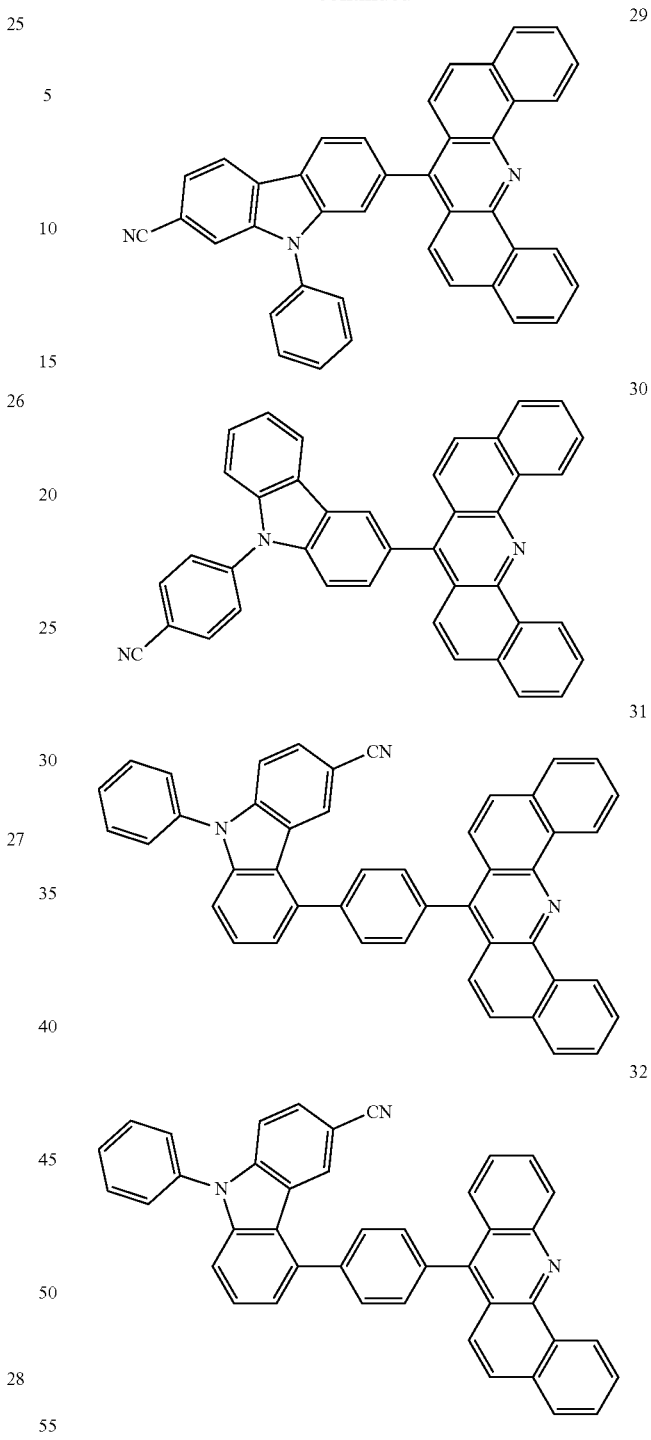

In an embodiment the compound of formula (I) has an energy gap LUMO-HOMO which is lower than 3.89 eV.

The object is further achieved by an organic electronic device comprising an organic semiconducting layer, wherein the organic semiconducting layer comprises the compound of general formula (I) as described herein.

The organic electronic device may further comprise a first electrode and a second electrode, wherein the organic semiconducting layer is arranged between the first electrode and the second electrode.

In the organic electronic device the organic semiconducting layer may be an emission layer. That is, according to one embodiment of the present invention, the organic electronic device comprises the compound of formula (I) in the emission layer thereof.

In a further embodiment, the organic semiconducting layer is a hole blocking layer. That is, in one embodiment of the present invention, the organic electronic device comprises the compound of formula (I) in a hole blocking layer thereof.

In this regard, it may be provided that the hole blocking layer does not comprise a dopant or an additive.

In a further embodiment, the organic semiconducting layer is an electron transport layer. That is, in this embodiment, the organic electronic device comprises a compound of formula (I) in an electron transport layer thereof.

In this regard, it may be provided that the electron transport layer further (in addition to the compound of formula (I)) comprises a dopant or an additive.

Suitable additives or dopants in this regard may be n-type additives or n-type dopants, such as LiQ, rare earth metals, alkali metals, alkaline earth metals, borates (CAS 14728-62-2), phenolates (such as CAS 1440864-50-5), phosphine imines (such as CAS 51870-56-5), guanidines (such as CAS 1623748-16-2), metal complexes as disclosed in US2009212280, heterocyclic compounds disclosed in US2007252140 etc.

In the organic electronic device, the organic semiconducting layer may further comprise at least one second compound besides the compound of formula (I). In this regard, it may be provided that the at least one second compound is a metal, a metal salt, a metal complex, a heterocyclic compound disclosed in US2007252140, an organic or metal-organic emitter compound or a mixture thereof. The metal complex may be an organic alkali metal complex or a complex disclosed in US2009212280. The organic alkali metal complex may be an alkali borate and/or phenolate and/or 8-hydroxyquinolinolato lithium.

The object is further achieved by a display device comprising the organic electronic device as defined herein.

The object is further achieved by a lighting device comprising the organic electronic device as defined herein.

The structures of the example part of the present application are most preferred.

Further Layers

In accordance with the invention, the organic electronic device may comprise, besides the layers already mentioned above, further layers. Exemplary embodiments of respective layers are described in the following:

Substrate

The substrate may be any substrate that is commonly used in manufacturing of, electronic devices, such as organic light-emitting diodes. If light is to be emitted through the substrate, the substrate shall be a transparent or semitransparent material, for example a glass substrate or a transparent plastic substrate. If light is to be emitted through the top surface, the substrate may be both a transparent as well as a non-transparent material, for example a glass substrate, a plastic substrate, a metal substrate or a silicon substrate.

Anode Electrode

Either a first electrode or a second electrode comprised in the inventive organic electronic device may be an anode electrode. The anode electrode may be formed by depositing or sputtering a material that is used to form the anode electrode. The material used to form the anode electrode may be a high work-function material, so as to facilitate hole injection. The anode material may also be selected from a low work function material (i.e. aluminum). The anode electrode may be a transparent or reflective electrode. Transparent conductive oxides, such as indium tin oxide (ITO), indium zinc oxide (IZO), tin-dioxide ($SnO_2$), aluminum zinc oxide (AIZO) and zinc oxide (ZnO), may be used to form the anode electrode. The anode electrode may also be formed using metals, typically silver (Ag), gold (Au), or metal alloys.

Hole Injection Layer

A hole injection layer (HIL) may be formed on the anode electrode by vacuum deposition, spin coating, printing, casting, slot-die coating, Langmuir-Blodgett (LB) deposition, or the like. When the HIL is formed using vacuum deposition, the deposition conditions may vary according to the compound that is used to form the HIL, and the desired structure and thermal properties of the HIL. In general, however, conditions for vacuum deposition may include a deposition temperature of 100° C. to 500° C., a pressure of 10-8 to 10-3 Torr (1 Torr equals 133.322 Pa), and a deposition rate of 0.1 to 10 nm/sec.

When the HIL is formed using spin coating or printing, coating conditions may vary according to the compound that is used to form the HIL, and the desired structure and thermal properties of the HIL. For example, the coating conditions may include a coating speed of about 2000 rpm to about 5000 rpm, and a thermal treatment temperature of about 80° C. to about 200° C. Thermal treatment removes a solvent after the coating is performed.

The HIL may be formed of any compound that is commonly used to form a HIL. Examples of compounds that may be used to form the HIL include a phthalocyanine compound, such as copper phthalocyanine (CuPc), 4,4',4"-tris (3-methylphenylphenylamino) triphenylamine (m-MTDATA), TDATA, 2T-NATA, polyaniline/dodecylbenzene-sulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate (PANI/PSS).

The HIL may comprise, or consist of, a p-type dopant and the p-type dopant may be selected from tetrafluoro-tetracyanoquinonedimethane (F4TCNQ), 2,2'-(perfluoronaphthalen-2,6-diylidene) dimalononitrile or 2,2',2"-(cyclopropane-1,2,3-triylidene)tris(2-(p-cyanotetrafluorophenyl) acetonitrile) but not limited hereto. The HIL may be selected from a hole-transporting matrix compound doped with a p-type dopant. Typical examples of known doped hole transport materials are: copper phthalocyanine (CuPc), which HOMO level is approximately −5.2 eV, doped with tetrafluoro-tetracyanoquinonedimethane (F4TCNQ), which LUMO level is about −5.2 eV; zinc phthalocyanine (ZnPc) (HOMO=−5.2 eV) doped with F4TCNQ; α-NPD (N,N'-Bis (naphthalen-1-yl)-N,N'-bis(phenyl)-benzidine) doped with F4TCNQ. α-NPD doped with 2,2'-(perfluoronaphthalen-2, 6-diylidene) dimalononitrile. The p-type dopant concentrations may be selected from 1 to 20 wt.-%, more preferably from 3 wt.-% to 10 wt.-%.

The thickness of the HIL may be in the range from about 1 nm to about 100 nm, and for example, from about 1 nm to about 25 nm. When the thickness of the HIL is within this range, the HIL may have excellent hole injecting characteristics, without a substantial penalty in driving voltage.

Hole Transport Layer

A hole transport layer (HTL) may be formed on the HIL by vacuum deposition, spin coating, slot-die coating, printing, casting, Langmuir-Blodgett (LB) deposition, or the like. When the HTL is formed by vacuum deposition or spin coating, the conditions for deposition and coating may be similar to those for the formation of the HIL. However, the conditions for the vacuum or solution deposition may vary, according to the compound that is used to form the HTL.

The HTL may be formed of any compound that is commonly used to form a HTL.

Compounds that can be suitably used are disclosed for example in Yasuhiko Shirota and Hiroshi Kageyama, Chem. Rev. 2007, 107, 953-101 and incorporated by reference. Examples of the compound that may be used to form the HTL are: carbazole derivatives, such as N-phenylcarbazole or polyvinylcarbazole; benzidine derivatives, such as N,N'-bis(3-methylphenyl)-N,N'-diphenyl-[1,1-biphenyl]-4,4'-diamine (TPD), or N,N'-di(naphthalen-1-yl)-N,N'-diphenyl benzidine (alpha-NPD); and triphenylamine-based compound, such as 4,4',4"-tris(N-carbazolyl)triphenylamine (TCTA). Among these compounds, TCTA can transport holes and inhibit excitons from being diffused into the EML.

The thickness of the HTL may be in the range of about 5 nm to about 250 nm, preferably, about 10 nm to about 200 nm, further about 20 nm to about 190 nm, further about 40 nm to about 180 nm, further about 60 nm to about 170 nm, further about 80 nm to about 160 nm, further about 100 nm to about 160 nm, further about 120 nm to about 140 nm.

When the thickness of the HTL is within this range, the HTL may have excellent hole transporting characteristics, without a substantial penalty in driving voltage.

Electron Blocking Layer

The function of an electron blocking layer (EBL) is to prevent electrons from being transferred from an emission layer to the hole transport layer and thereby confine electrons to the emission layer. Thereby, efficiency, operating voltage and/or lifetime are improved. Typically, the electron blocking layer comprises a triarylamine compound. The triarylamine compound may have a LUMO level closer to vacuum level than the LUMO level of the hole transport layer. The electron blocking layer may have a HOMO level that is further away from vacuum level compared to the HOMO level of the hole transport layer. The thickness of the electron blocking layer may be selected between 2 and 20 nm.

If the electron blocking layer has a high triplet level, it may also be described as triplet control layer.

The function of the triplet control layer is to reduce quenching of triplets if a phosphorescent green or blue emission layer is used. Thereby, higher efficiency of light emission from a phosphorescent emission layer can be achieved. The triplet control layer is selected from compounds with a triplet level above the triplet level of the phosphorescent emitter in the adjacent emission layer. Suitable compounds for the triplet control layer, in particular the triarylamine compounds, are described in EP 2 722 908 A1.

Emission Layer (EML)

The EML may be formed on the HTL by vacuum deposition, spin coating, slot-die coating, printing, casting, LB deposition, or the like. When the EML is formed using vacuum deposition or spin coating, the conditions for deposition and coating may be similar to those for the formation of the HIL. However, the conditions for deposition and coating may vary, according to the compound that is used to form the EML.

It may be provided that the emission layer comprises a compound of Formula (I).

The EML may be formed of a combination of host materials and emitter dopants. The EML may comprise a single host material or a plurality of host materials. The EML may comprise a single emitter dopant or a plurality of emitter dopants. Examples of the host materials are Alq3, 4,4'-N,N'-dicarbazole-biphenyl (CBP), poly(n-vinylcarbazole) (PVK), 9,10-di(naphthalene-2-yl)anthracene (ADN), 4,4',4"-tris(carbazol-9-yl)-triphenylamine(TCTA), 1,3,5-tris (N-phenylbenzimidazole-2-yl)benzene (TPBI), 3-tert-butyl-9,10-di-2-naphthylanthracenee (TBADN), distyrylarylene (DSA) and bis(2-(2-hydroxyphenyl)benzo-thiazolate)zinc (Zn(BTZ)2) or a compound of Formula (I).

In case the EML comprises a plurality of host materials to form a host mixture the amount of each host material in the mixture of host materials may vary between 0.01 and 99.99 parts by weight.

The emitter dopant may be a phosphorescent or fluorescent emitter. Phosphorescent emitters and emitters which emit light via a thermally activated delayed fluorescence (TADF) mechanism may be preferred due to their higher efficiency. The emitter may be a small molecule or a polymer.

Examples of red emitter dopants are PtOEP, Ir(piq)3, and Btp2Ir(acac), but are not limited thereto. These compounds are phosphorescent emitters, however, fluorescent red emitter dopants could also be used.

Examples of phosphorescent green emitter dopants are Ir(ppy)3 (ppy=phenylpyridine), Ir(ppy)2(acac), Ir(mpyp)3.

Examples of phosphorescent blue emitter dopants are F2Irpic, (F2ppy)2Ir(tmd) and Ir(dfppz)3 and ter-fluorene. 4,4'-bis(4-diphenyl amiostyryl)biphenyl (DPAVBi), 2,5,8,11-tetra-tert-butyl perylene (TBPe) are examples of fluorescent blue emitter dopants.

The amount of the emitter dopant may be in the range from about 0.01 to about 50 parts by weight, based on 100 parts by weight of the host or host mixture. Alternatively, the emission layer may consist of a light-emitting polymer. The EML may have a thickness of about 10 nm to about 100 nm, for example, from about 20 nm to about 60 nm. When the thickness of the EML is within this range, the EML may have excellent light emission, without a substantial penalty in driving voltage.

Hole Blocking Layer (HBL)

A hole blocking layer (HBL) may be formed on the EML, by using vacuum deposition, spin coating, slot-die coating, printing, casting, LB deposition, or the like, in order to prevent the diffusion of holes into the ETL. When the EML comprises a phosphorescent dopant, the HBL may have also a triplet exciton blocking function. The hole blocking layer may be the inventive organic semiconducting layer comprising or consisting of the inventive compound represented by the general Formula (I) as defined above. The HBL may be the layer (or one of several layers) comprising the compound of formula (I).

The HBL may also be named auxiliary ETL or α-ETL.

When the HBL is formed using vacuum deposition or spin coating, the conditions for deposition and coating may be similar to those for the formation of the HIL. However, the conditions for deposition and coating may vary, according to the compound that is used to form the HBL. Any compound that is commonly used to form a HBL may be used. Examples of compounds for forming the HBL include oxadiazole derivatives, triazine derivatives, triazole derivatives, and phenanthroline derivatives.

The HBL may have a thickness in the range from about 5 nm to about 100 nm, for example, from about 10 nm to about 30 nm. When the thickness of the HBL is within this range, the HBL may have excellent hole-blocking properties, without a substantial penalty in driving voltage.

Electron Transport Layer (ETL)

The OLED according to the present invention may comprise an electron transport layer (ETL). In accordance with the invention, the electron transport layer may be the inventive organic semiconducting layer comprising the inventive compound represented by the general Formula (I) as defined above. In an embodiment the ETL may consist of a compound of Formula (I).

According to various embodiments the OLED may comprise an electron transport layer or an electron transport layer stack comprising at least a first electron transport layer and at least a second electron transport layer.

By suitably adjusting energy levels of particular layers of the ETL, the injection and transport of the electrons may be controlled, and the holes may be efficiently blocked. Thus, the OLED may have long lifetime.

The electron transport layer of the organic electronic device may comprise the compound represented by general Formula (I) as defined above as the organic electron transport matrix (ETM) material. The electron transport layer may comprise, besides the compound represented by the general Formula (I), further ETM materials known in the art. Likewise, the electron transport layer may comprise as the only electron transport matrix material the compound represented by general Formula (I). In case that the inventive organic electronic device comprises more than one electron transport layers, the compound represented by the general Formula (I) may be comprised in only one of the electron transport layers, in more than one of the electron transport layers or in all of the electron transport layers. In accordance with the invention, the electron transport layer may comprise, besides the ETM material, at least one additive as defined herein.

Further, the electron transport layer may comprise one or more n-type dopants. The additive may be an n-type dopant. The additive can be alkali metal, alkali metal compound, alkaline earth metal, alkaline earth metal compound, transition metal, transition metal compound or a rare earth metal. In another embodiment, the metal can be one selected from a group consisting of Li, Na, K, Rb, Cs, Mg, Ca, Sr, Ba, La, Ce, Sm, Eu, Tb, Dy, and Yb. In another emdodiment, the n-type dopant can be one selected from a group consisting of Cs, K, Rb, Mg, Na, Ca, Sr, Eu and Yb. In an embodiment the alkali metal compound may be 8-Hydroxyquinolinolato-lithium (LiQ), Lithium tetra(1H-pyrazol-1-yl)borate or Lithium 2-(diphenylphosphoryl)phenolate. Suitable compounds for the ETM (which may be used in addition to the inventive compound represented by the general Formula (I) as defined above) are not particularly limited. In one embodiment, the electron transport matrix compounds consist of covalently bound atoms. Preferably, the electron transport matrix compound comprises a conjugated system of at least 6, more preferably of at least 10 delocalized electrons. In one embodiment, the conjugated system of delocalized electrons may be comprised in aromatic or heteroaromatic structural moieties, as disclosed e.g. in documents EP 1 970 371 A1 or WO 2013/079217 A1.

Electron Injection Layer (EIL)

An optional EIL, which may facilitates injection of electrons from the cathode, may be formed on the ETL, preferably directly on the electron transport layer. Examples of materials for forming the EIL include lithium 8-hydroxyquinolinolate (LiQ), LiF, NaCl, CsF, Li2O, BaO, Ca, Ba, Yb, Mg which are known in the art. Deposition and coating conditions for forming the EIL are similar to those for formation of the HIL, although the deposition and coating conditions may vary, according to the material that is used to form the EIL. The EIL may be the organic semiconducting layer comprising the compound of Formula (I).

The thickness of the EIL may be in the range from about 0.1 nm to about 10 nm, for example, in the range from about 0.5 nm to about 9 nm. When the thickness of the EIL is within this range, the EIL may have satisfactory electron-injecting properties, without a substantial penalty in driving voltage.

Cathode Electrode

The cathode electrode is formed on the EIL, if present. The cathode electrode may be formed of a metal, an alloy, an electrically conductive compound, or a mixture thereof. The cathode electrode may have a low work function. For example, the cathode electrode may be formed of lithium (Li), magnesium (Mg), aluminum (Al), aluminum (Al)-lithium (Li), calcium (Ca), barium (Ba), ytterbium (Yb), magnesium (Mg)-indium (In), magnesium (Mg)-silver (Ag), or the like. Alternatively, the cathode electrode may be formed of a transparent conductive oxide, such as ITO or IZO.

The thickness of the cathode electrode may be in the range from about 5 nm to about 1000 nm, for example, in the range from about 10 nm to about 100 nm. When the thickness of the cathode electrode is in the range from about 5 nm to about 50 nm, the cathode electrode may be transparent or semitransparent even if formed by a metal or metal alloy.

It is to be understood that the cathode electrode is not part of an electron injection layer or the electron transport layer.

Charge Generation Layer

The charge generation layer (CGL) may comprise a p-type and an n-type layer. An interlayer may be arranged between the p-type layer and the n-type layer. The CGL may comprise the compound represented by general Formula (I).

Typically, the charge generation layer is a pn junction joining an n-type charge generation layer (electron generating layer) and a hole generating layer. The n-side of the pn junction generates electrons and injects them into the layer which is adjacent in the direction to the anode. Analogously, the p-side of the p-n junction generates holes and injects them into the layer which is adjacent in the direction to the cathode.

Charge generating layers may be used in tandem devices, for example, in tandem OLEDs comprising, between two electrodes, two or more emission layers. In a tandem OLED comprising two emission layers, the n-type charge generation layer provides electrons for the first light emission layer arranged near the anode, while the hole generating layer provides holes to the second light emission layer arranged between the first emission layer and the cathode.

Suitable matrix materials for the hole generating layer may be materials conventionally used as hole injection and/or hole transport matrix materials. Also, p-type dopant used for the hole generating layer can employ conventional materials. For example, the p-type dopant can be one selected from a group consisting of tetrafluore-7,7,8,8-tetracyanoquinodimethane (F4-TCNQ), derivatives of tetracyanoquinodimethane, radialene derivatives, iodine, FeCl3, FeF3, and SbCl5. Also, the host can be one selected from a group consisting of N,N'-di(naphthalen-1-yl)-N,N-diphenyl-benzidine (NPB), N,N'-diphenyl-N,N'-bis(3-methylphenyl)-1,1-biphenyl-4,4'-diamine (TPD) and N,N',N'-tetranaphthyl-benzidine (TNB). The p-type charge generation layer may consist of CNHAT.

The n-type charge generating layer may be the layer comprising the compound of Formula (I). The n-type charge generation layer can be layer of a neat n-type dopant, for example of an electropositive metal, or can consist of an organic matrix material doped with the n-type dopant. In one embodiment, the n-type dopant can be alkali metal, alkali metal compound, alkaline earth metal, alkaline earth metal compound, a transition metal, a transition metal compound or a rare earth metal. In another embodiment, the metal can be one selected from a group consisting of Li, Na, K, Rb, Cs, Mg, Ca, Sr, Ba, La, Ce, Sm, Eu, Tb, Dy, and Yb. More specifically, the n-type dopant can be one selected from a group consisting of Cs, K, Rb, Mg, Na, Ca, Sr, Eu and Yb. Suitable matrix materials for the electron generating layer may be the materials conventionally used as matrix materials for electron injection or electron transport layers. The matrix material can be for example one selected from a group consisting of triazine compounds, hydroxyquinoline derivatives like tris(8-hydroxyquinoline)aluminum, benzazole derivatives, and silole derivatives.

The hole generating layer is arranged in direct contact to the n-type charge generation layer.

Organic Light-Emitting Diode (OLED)

The organic electronic device according to the invention may be an organic light-emitting device.

According to one aspect of the present invention, there is provided an organic light-emitting diode (OLED) comprising: a substrate; an anode electrode formed on the substrate; a hole injection layer, a hole transport layer, an emission layer, an organic semiconducting layer comprising a compound of formula (I) or consisting of a compound of Formula (I) and a cathode electrode.

According to another aspect of the present invention, there is provided an OLED comprising: a substrate; an anode electrode formed on the substrate; a hole injection layer, a hole transport layer, an electron blocking layer, an emission layer, a hole blocking layer, an organic semiconducting layer comprising a compound of formula (I) or consisting of a compound of Formula (I) and a cathode electrode.

According to another aspect of the present invention, there is provided an OLED comprising: a substrate; an anode electrode formed on the substrate; a hole injection layer, a hole transport layer, an electron blocking layer, an emission layer, a hole blocking layer, an organic semiconducting layer comprising a compound of Formula (I) or consisting of a compound of Formula (I), an electron injection layer, and a cathode electrode.

According to various embodiments of the present invention, there may be provided OLEDs layers arranged between the above mentioned layers, on the substrate or on the top electrode.

According to one aspect, the OLED can comprise a layer structure of a substrate that is adjacently arranged to an anode electrode, the anode electrode is adjacently arranged to a first hole injection layer, the first hole injection layer is adjacently arranged to a first hole transport layer, the first hole transport layer is adjacently arranged to a first electron blocking layer, the first electron blocking layer is adjacently arranged to a first emission layer, the first emission layer is adjacently arranged to a first electron transport layer, the first electron transport layer is adjacently arranged to an n-type charge generation layer, the n-type charge generation layer is adjacently arranged to a hole generating layer, the hole generating layer is adjacently arranged to a second hole transport layer, the second hole transport layer is adjacently arranged to a second electron blocking layer, the second electron blocking layer is adjacently arranged to a second emission layer, between the second emission layer and the cathode electrode an optional electron transport layer and/or an optional injection layer are arranged.

The organic semiconducting layer according to the invention may be an emission layer, a hole blocking layer, an electron transport layer, a first electron transport layer, an n-type charge generation layer and/or a second electron transport layer.

For example, the OLED (10) according to FIG. 2 may be formed by a process, wherein on a substrate (110), an anode (120), a hole injection layer (130), a hole transport layer (140), an electron blocking layer (145), an emission layer (150), a hole blocking layer (155), an electron transport layer (160), an electron injection layer (180) and the cathode electrode (190) are subsequently formed in that order.

Organic Electronic Device

An organic electronic device according to the invention comprises an organic semiconducting layer comprising a compound according to Formula (I) or consisting of a compound of Formula (I).

An organic electronic device according to one embodiment may include a substrate, an anode layer, an organic semiconducting layer comprising a compound of Formula (I) or consisting of a compound of Formula (I) and a cathode layer.

An organic electronic device according to one embodiment comprises at least one organic semiconducting layer comprising at least one compound of Formula (I) or consisting of a compound of Formula (I), at least one anode layer, at least one cathode layer and at least one emission layer, wherein the organic semiconducting layer is preferably arranged between the emission layer and the cathode layer.

An organic light-emitting diode (OLED) according to the invention may include an anode, a hole transport layer (HTL), an emission layer (EML), an electron transport layer (ETL) comprising at least one compound of Formula (I), and a cathode, which are sequentially stacked on a substrate. In this regard, the HTL, the EML, and the ETL are thin films formed from organic compounds.

An organic electronic device according to one embodiment can be a light emitting device, thin film transistor, a battery, a display device or a photovoltaic cell, and preferably a light emitting device.

According to another aspect of the present invention, there is provided a method of manufacturing an organic electronic device, the method using:

at least one deposition source, preferably two deposition sources and more preferred at least three deposition sources.

The methods for deposition that can be suitable comprise:

deposition via vacuum thermal evaporation;

deposition via solution processing, preferably the processing is selected from spin-coating, printing, casting; and/or slot-die coating.

According to various embodiments of the present invention, there is provided a method using:

a first deposition source to release the compound of Formula (I) according to the invention, and a second deposition source to release a metal, a metal complex, an organo-metallic compound, a metal salt or an alkali or alkaline earth metal complex; alternatively an organic alkali or alkaline earth metal complex; alternatively 8-hydroxyquinolinolato lithium or alkali borate;

the method comprising the steps of forming the organic semiconducting layer; whereby for an organic light-emitting diode (OLED):

the organic semiconducting layer is formed by releasing the compound of Formula (I) according to the invention from the first deposition source and a metal, a metal complex, an organo-metallic compound, a metal salt or an alkali or alkaline earth metal complex; alternatively an organic alkali or alkaline earth metal complex; alternatively 8-hydroxyquinolinolato lithium or alkali borate, from the second deposition source.

According to various embodiments of the present invention, the method may further include forming on the anode electrode, an emission layer and at least one layer selected from the group consisting of forming a hole injection layer, forming a hole transport layer, or forming a hole blocking layer, between the anode electrode and the first electron transport layer.

According to various embodiments of the present invention, the method may further include the steps for forming an organic light-emitting diode (OLED), wherein
on a substrate a first anode electrode is formed,
on the first anode electrode an emission layer is formed,
on the emission layer an electron transport layer stack is formed, optionally a hole blocking layer is formed on the emission layer and an organic semiconducting layer is formed,
and finally a cathode electrode is formed,
optional a hole injection layer, a hole transport layer, and a hole blocking layer, formed in that order between the first anode electrode and the emission layer,
optional an electron injection layer is formed between the organic semiconducting layer and the cathode electrode.

According to various embodiments of the present invention, the method may further comprise forming an electron injection layer on the organic semiconducting layer. However, according to various embodiments of the OLED of the present invention, the OLED may not comprise an electron injection layer.

According to various embodiments, the OLED may have the following layer structure, wherein the layers having the following order:
anode, hole injection layer, first hole transport layer, second hole transport layer, emission layer, optional hole blocking layer, organic semiconducting layer comprising a compound of Formula (I) according to the invention, optional electron injection layer, and cathode, or
anode, hole injection layer, first hole transport layer, second hole transport layer, organic semiconducting layer comprising a compound of Formula (I) according to the invention, optional hole blocking layer, first electron transport layer, optional electron injection layer, and cathode, or
anode, hole injection layer, first hole transport layer, second hole transport layer, emission layer, organic semiconducting layer comprising a compound of Formula (I) according to the invention, first electron transport layer, optional electron injection layer, and cathode.

According to another aspect of the invention, it is provided an electronic device comprising at least one organic light emitting device according to any embodiment described throughout this application, preferably, the electronic device comprises the organic light emitting diode in one of embodiments described throughout this application. More preferably, the electronic device is a display device.

In one embodiment, the organic electronic device according to the invention comprising an organic semiconducting layer comprising a compound according to Formula (I) or consisting of a compound of Formula (I) may further comprise a layer comprising a radialene compound and/or a quinodimethane compound.

In one embodiment, the radialene compound and/or the quinodimethane compound may be substituted with one or more halogen atoms and/or with one or more electron withdrawing groups. Electron withdrawing groups can be selected from nitrile groups, halogenated alkyl groups, alternatively from perhalogenated alkyl groups, alternatively from perfluorinated alkyl groups. Other examples of electron withdrawing groups may be acyl, sulfonyl groups or phosphoryl groups.

Alternatively, acyl groups, sulfonyl groups and/or phosphoryl groups may comprise halogenated and/or perhalogenated hydrocarbyl. In one embodiment, the perhalogenated hydrocarbyl may be a perfluorinated hydrocarbyl. Examples of a perfluorinated hydrocarbyl can be perfluormethyl, perfluorethyl, perfluorpropyl, perfluorisopropyl, perfluorobutyl, perfluorophenyl, perfluorotolyl; examples of sulfonyl groups comprising a halogenated hydrocarbyl may be trifluoromethylsulfonyl, pentafluoroethylsulfonyl, pentafluorophenylsulfonyl, heptafluoropropylsufonyl, nonafluorobutylsulfonyl, and like.

In one embodiment, the radialene and/or the quinodimethane compound may be comprised in a hole injection, hole transporting and/or a hole generation layer.

In one embodiment, the radialene compound may have Formula (XX) and/or the quinodimethane compound may have Formula (XXIa) or (XXIb):

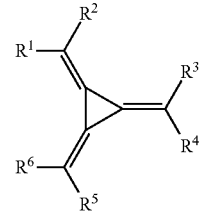
(XX)

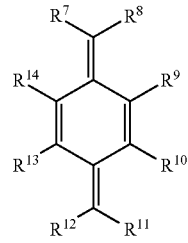
(XXIa)

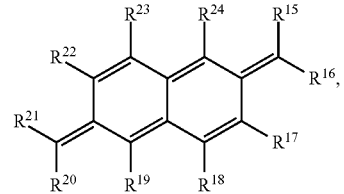
(XXIb)

wherein $R^1$, $R^2$, $R^3$, $R^4$, $R^5$, $R^6$, $R^7$, $R^8$, $R^{11}$, $R^{12}$, $R^{15}$, $R^{16}$, $R^{20}$, $R^{21}$ are independently selected from above mentioned electron withdrawing groups and $R^9$, $R^{10}$, $R^{13}$, $R^{14}$, $R^{17}$, $R^{18}$, $R^{19}$, $R^{22}$, $R^{23}$ and $R^{24}$ are independently selected from H, halogen and above mentioned electron withdrawing groups.

Hereinafter, the embodiments are illustrated in more detail with reference to examples. However, the present disclosure is not limited to the following examples. Reference will now be made in detail to the exemplary aspects.

Details and Definitions of the Invention

The term "fused rings" is used herein refers to a binding situation where two adjacent $R^1$ to $R^{11}$, for example, $R^1$ and $R^2$; or $R^2$ and $R^3$; $R^3$ and $R^4$ form together a ring fused to the remaining part of the structure having the Formula (I).

In the present specification, when a definition is not otherwise provided, an "alkyl group" may refer to an aliphatic hydrocarbon group. The alkyl group may refer to "a saturated alkyl group" without any double bond or triple bond. The term "alkyl" as used herein shall encompass linear as well as branched and cyclic alkyl. For example, $C_3$-alkyl may be selected from n-propyl and iso-propyl. Likewise, $C_4$-alkyl encompasses n-butyl, sec-butyl and t-butyl. Likewise, $C_6$-alkyl encompasses n-hexyl and cyclohexyl.

The subscribed number n in $C_n$ relates to the total number of carbon atoms in the respective alkyl, arylene, heteroarylene or aryl group.

The term "aryl" or "arylene" as used herein shall encompass phenyl ($C_6$-aryl), fused aromatics, such as naphthalene, anthracene, phenanthracene, tetracene etc. Further encompassed are biphenyl and oligo- or polyphenyls, such as terphenyl etc. Further encompassed shall be any further aromatic hydrocarbon substituents, such as fluorenyl etc. "Arylene" respectively "heteroarylene", referres to groups to which two further moieties are attached. In the present specification the term "aryl group" or "arylene group" may refer to a group comprising at least one hydrocarbon aromatic moiety, and all the elements of the hydrocarbon aromatic moiety may have p-orbitals which form conjugation, for example a phenyl group, a naphtyl group, an anthracenyl group, a phenanthrenyl group, a pyrenyl group, a fluorenyl group and the like. The aryl or arylene group may include a monocyclic or fused ring polycyclic (i.e., rings sharing adjacent pairs of carbon atoms) functional group.

The term "heteroaryl" as used herein refers to aryl groups in which at least one carbon atom is substituted with a heteroatom, preferably selected from N, O, S, B or Si.

The subscripted number n in $C_n$-heteroaryl merely refers to the number of carbon atoms excluding the number of heteroatoms. In this context, it is clear that a $C_3$ heteroarylene group is an aromatic compound comprising three carbon atoms, such as pyrazol, imidazole, oxazole, thiazole and the like.

The term "heteroaryl" may refer to aromatic heterocycles with at least one heteroatom, and all the elements of the hydrocarbon heteroaromatic moiety may have p-orbitals which form conjugation. The heteroatom may be selected from N, O, S, B, Si, P, Se, preferably from N, O and S. A heteroarylene ring may comprise at least 1 to 3 heteroatoms. Preferably a heteroarylene ring may comprise at least 1 to 3 heteroatoms individually selected from N, S and/or O.

The term "heteroaryl" as used herewith shall encompass pyridine, quinoline, quinazoline, pyridine, triazine, benzimidazole, benzothiazole, benzo[4,5]thieno[3,2-d]pyrimidine, carbazole, xanthene, phenoxazine, benzoacridine, dibenzoacridine and the like.

In the present specification, the single bond refers to a direct bond.

The term "fluorinated" as used herein refers to a hydrocarbon group in which at least one of the hydrogen atoms comprised in the hydrocarbon group is substituted by a fluorine atom. Fluorinated groups in which all of the hydrogen atoms thereof are substituted by fluorine atoms are referred to as perfluorinated groups and are particularly addressed by the term "fluorinated".

In terms of the invention, a group is "substituted with" another group if one of the hydrogen atoms comprised in this group is replaced by another group, wherein the other group is the substituent.

In terms of the invention, the expression "between" with respect to one layer being between two other layers does not exclude the presence of further layers which may be arranged between the one layer and one of the two other layers. In terms of the invention, the expression "in direct contact" with respect to two layers being in direct contact with each other means that no further layer is arranged between those two layers. One layer deposited on the top of another layer is deemed to be in direct contact with this layer.

With respect to the inventive organic semiconducting layer as well as with respect to the inventive compound, the compounds mentioned in the experimental part are most preferred.

The inventive organic electronic device may be an organic electroluminescent device (OLED) an organic photovoltaic device (OPV), a lighting device, or an organic field-effect transistor (OFET). A lighting device may be any of the devices used for illumination, irradiation, signaling, or projection. They are correspondingly classified as illuminating, irradiating, signaling, and projecting devices. A lighting device usually consists of a source of optical radiation, a device that transmits the radiant flux into space in the desired direction, and a housing that joins the parts into a single device and protects the radiation source and light-transmitting system against damage and the effects of the surroundings.

According to another aspect, the organic electroluminescent device according to the present invention may comprise more than one emission layer, preferably two or three emission layers. An OLED comprising more than one emission layer is also described as a tandem OLED or stacked OLED.

The organic electroluminescent device (OLED) may be a bottom- or top-emission device.

Another aspect is directed to a device comprising at least one organic electroluminescent device (OLED).

A device comprising organic light-emitting diodes is for example a display or a lighting panel.

In the present invention, the following defined terms, these definitions shall be applied, unless a different definition is given in the claims or elsewhere in this specification.

In the context of the present specification the term "different" or "differs" in connection with the matrix material means that the matrix material differs in their structural Formula.

The terms "OLED" and "organic light-emitting diode" are simultaneously used and have the same meaning. The term "organic electroluminescent device" as used herein may comprise both organic light emitting diodes as well as organic light emitting transistors (OLETs).

As used herein, "weight percent", "wt.-%", "percent by weight", "% by weight", parts by weight and variations thereof refer to a composition, component, substance or agent as the weight of that component, substance or agent of the respective electron transport layer divided by the total weight of the respective electron transport layer thereof and multiplied by 100. It is under-stood that the total weight percent amount of all components, substances and agents of the respective electron transport layer and electron injection layer are selected such that it does not exceed 100 wt.-%.

As used herein, "volume percent", "vol.-%", "percent by volume", "% by volume", and variations thereof refer to a composition, component, substance or agent as the volume of that component, substance or agent of the respective electron transport layer divided by the total volume of the respective electron transport layer thereof and multiplied by 100. It is understood that the total volume percent amount of all components, substances and agents of the cathode layer are selected such that it does not exceed 100 vol.-%.

All numeric values are herein assumed to be modified by the term "about", whether or not explicitly indicated. As used herein, the term "about" refers to variation in the numerical quantity that can occur. Whether or not modified by the term "about" the claims include equivalents to the quantities.

It should be noted that, as used in this specification and the appended claims, the singular forms "a", "an", and "the" include plural referents unless the content clearly dictates otherwise.

The term "free of", "does not contain", "does not comprise" does not exclude impurities. Impurities have no technical effect with respect to the object achieved by the present invention.

In the context of the present specification the term "essentially non-emissive" or "non-emissive" means that the contribution of the compound or layer to the visible emission spectrum from the device is less than 10%, preferably less than 5% relative to the visible emission spectrum. The visible emission spectrum is an emission spectrum with a wavelength of about ≥380 nm to about ≤780 nm.

Preferably, the organic semiconducting layer comprising the compound of Formula I is essentially non-emissive or non-emitting.

The operating voltage, also named U, is measured in Volt (V) at 10 milliAmpere per square centimeter (mA/cm2).

The candela per Ampere efficiency, also named cd/A efficiency is measured in candela per ampere at to milliAmpere per square centimeter (mA/cm2).

The external quantum efficiency, also named EQE, is measured in percent (%).

The color space is described by coordinates CIE-x and CIE-y (International Commission on Illumination 1931). For blue emission the CIE-y is of particular importance. A smaller CIE-y denotes a deeper blue color.

The highest occupied molecular orbital, also named HOMO, and lowest unoccupied molecular orbital, also named LUMO, are measured in electron volt (eV).

The term "OLED", "organic light emitting diode", "organic light emitting device", "organic optoelectronic device" and "organic light-emitting diode" are simultaneously used and have the same meaning.

The term "life-span" and "lifetime" are simultaneously used and have the same meaning.

The anode electrode and cathode electrode may be described as anode electrode/cathode electrode or anode electrode/cathode electrode or anode electrode layer/cathode electrode layer.

Room temperature, also named ambient temperature, is 23° C.

BRIEF DESCRIPTION OF THE DRAWINGS

These and/or other aspects and advantages of the present invention will become apparent and more readily appreciated from the following description of the exemplary embodiments, taken in conjunction with the accompanying drawings, of which.

DETAILED DESCRIPTION

Figure 1:
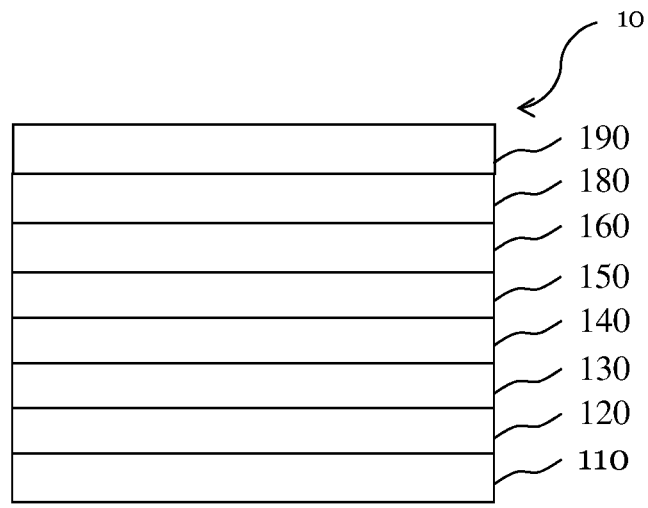
FIG. 1 is a schematic sectional view of an organic light-emitting diode (OLED), according to an exemplary embodiment of the present invention.

Reference will now be made in detail to the exemplary embodiments of the present invention, examples of which are illustrated in the accompanying drawings, wherein like reference numerals refer to the like elements throughout. The exemplary embodiments are described below, in order to explain the aspects of the present invention, by referring to the figures.

Herein, when a first element is referred to as being formed or disposed "on" or "onto" a second element, the first element can be disposed directly on the second element, or one or more other elements may be disposed there between. When a first element is to referred to as being formed or disposed "directly on" or "directly onto" a second element, no other elements are disposed there between.

FIG. 1 is a schematic sectional view of an organic light-emitting diode (OLED) 100, according to an exemplary embodiment of the present invention. The OLED 100 includes a substrate 110, an anode 120, a hole injection layer (HIL) 130, a hole transport layer (HTL) 140, an emission layer (EML) 150, an electron transport layer (ETL) 160. The electron transport layer (ETL) 160 is formed on the EML 150. Onto the electron transport layer (ETL) 160, an electron injection layer (EIL) 180 is disposed. The cathode 190 is disposed directly onto the electron injection layer (EIL) 180.

Instead of a single electron transport layer 160, optionally an electron transport layer stack (ETL) can be used.

Figure 2:
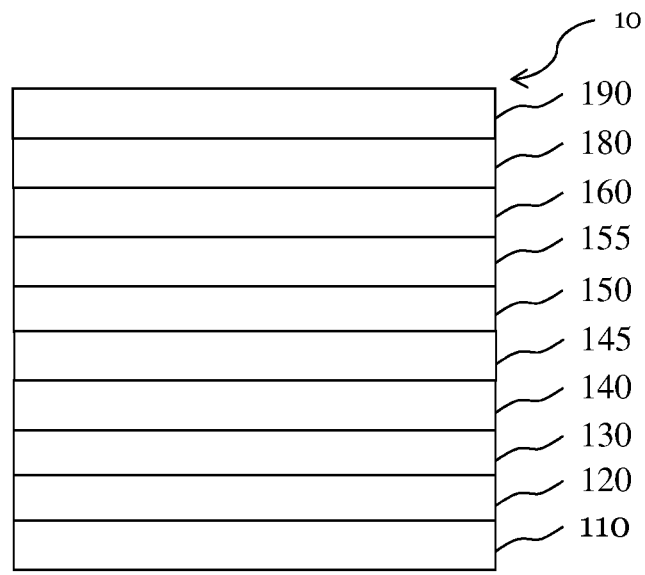
FIG. 2 is a schematic sectional view of an OLED, according to an exemplary embodiment of the present invention.

FIG. 2 is a schematic sectional view of an OLED 100, according to another exemplary embodiment of the present invention. FIG. 2 differs from FIG. 1 in that the OLED 100 of FIG. 2 comprises an electron blocking layer (EBL) 145 and a hole blocking layer (HBL) 155.

Referring to FIG. 2, the OLED 100 includes a substrate 110, an anode 120, a hole injection layer (HIL) 130, a hole transport layer (HTL) 140, an electron blocking layer (EBL) 145, an emission layer (EML) 150, a hole blocking layer (HBL) 155, an electron transport layer (ETL) 160, an electron injection layer (EIL) 180 and a cathode electrode 190.

Preferably, the organic semiconducting layer comprising a compound of Formula (I) or consisting of a compound of Formula (I) may be an EML, an HBL or an ETL.

Figure 3:
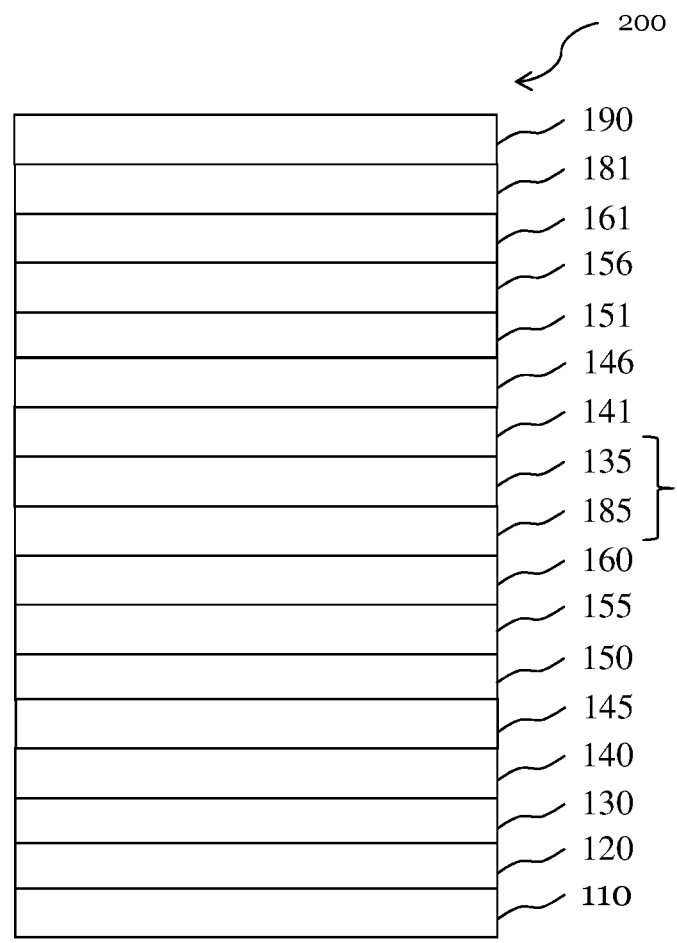
FIG. 3 is a schematic sectional view of a tandem OLED comprising a charge generation layer, according to an exemplary embodiment of the present invention.

FIG. 3 is a schematic sectional view of a tandem OLED 200, according to another exemplary embodiment of the present invention. FIG. 3 differs from FIG. 2 in that the OLED 100 of FIG. 3 further comprises a charge generation layer (CGL) and a second emission layer (151).

Referring to FIG. 3, the OLED 200 includes a substrate 110, an anode 120, a first hole injection layer (HIL) 130, a first hole transport layer (HTL) 140, a first electron blocking layer (EBL) 145, a first emission layer (EML) 150, a first hole blocking layer (HBL) 155, a first electron transport layer (ETL) 160, an n-type charge generation layer (n-type CGL) 185, a hole generating layer (p-type charge generation layer; p-type GCL) 135, a second hole transport layer (HTL) 141, a second electron blocking layer (EBL) 146, a second emission layer (EML) 151, a second hole blocking layer (EBL) 156, a second electron transport layer (ETL) 161, a second electron injection layer (EIL) 181 and a cathode 190.

Preferably, the organic semiconducting layer comprising a compound of Formula (I) or consisting of a compound of Formula (I) may be the first EML, first HBL, first ETL, n-type CGL and/or second EML, second HBL, second ETL.

While not shown in FIG. 1, FIG. 2 and FIG. 3, a sealing layer may further be formed on the cathode electrodes 190, in order to seal the OLEDs 100 and 200. In addition, various other modifications may be applied thereto.

Hereinafter, one or more exemplary embodiments of the present invention will be described in detail with, reference to the following examples. However, these examples are not intended to limit the purpose and scope of the one or more exemplary embodiments of the present invention.

Experimental Part

The invention is furthermore illustrated by the following examples which are illustrative only and non-binding.

Synthesis of Compounds of Formula (I)

9-(3-(dibenzo[c,h]acridin-7-yl)phenyl)-9H-carbazole-3-carbonitrile (Compound 5)

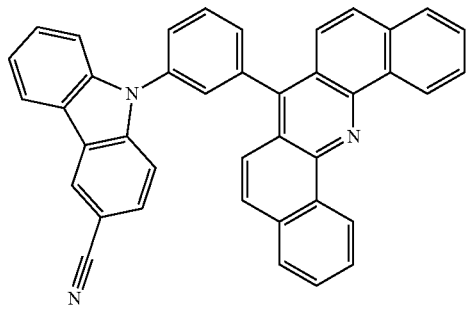 [SMILES: N#Cc1ccc2c(c1)c1ccccc1n2-c1cccc(-c2c3ccc4ccccc4c3nc3c2ccc2ccccc23)c1]

A flask was flushed with nitrogen and charged with 7-chlorodibenzo[c,h]acridine (12 g, 38.4 mmol), 9-(3-(4,4,5,5-tetramethyl-1,3,2-dioxaborolan-2-yl)phenyl)-9H-carbazole-3-carbonitrile (15.9 g, 40 mmol), Pd(PPh$_3$)$_4$ (1.3 g, 1.15 mmol), and K$_2$CO$_3$ (15.9 g, 115 mmol). A mixture of deaerated 1,4-dioxane/water (3:1, 240 mL) was added and the reaction mixture was heated to 95° C. under a nitrogen atmosphere for 16 h. After cooling down to room temperature, the formed precipitate was collected by suction filtration and washed with 1,4-dioxane, water and methanol. The obtained solid was dissolved in hot dichloromethane and filtered through a pad of silica gel. After rinsing with additional hot dichloromethane, the filtrate was concentrated under reduced pressure and n-hexane was added. The obtained precipitate was collected by suction filtration and washed with n-hexane. After drying, 19.2 g (91%) of a pale yellow solid were obtained. HPLC/ESI-MS: 100%, m/z=546 ([M+H]$^+$).

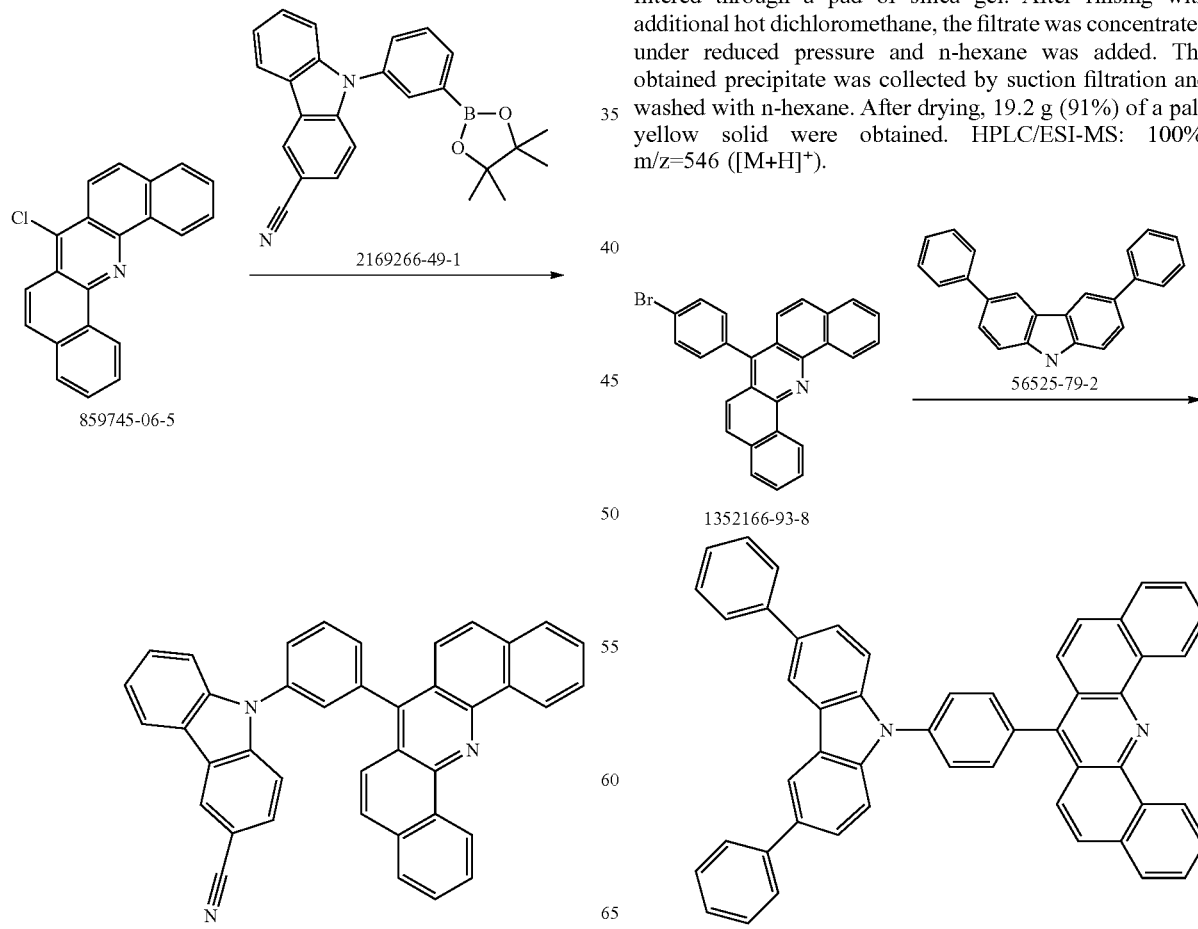

7-(4-(3,6-diphenyl-9H-carbazol-9-yl)phenyl)dibenzo[c,h]acridine (Compound 4)

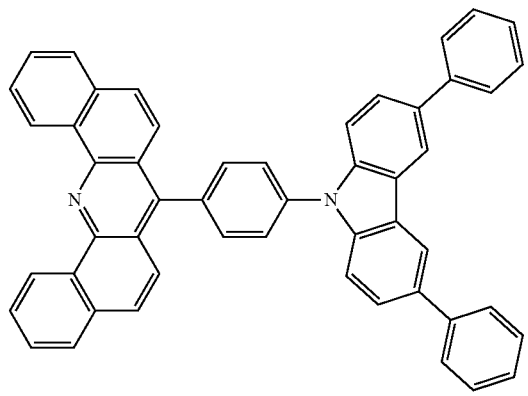 [SMILES: c1ccc(-c2ccc3c(c2)c2cc(-c4ccccc4)ccc2n3-c2ccc(-c3c4ccc5ccccc5c4nc4c3ccc3ccccc34)cc2)cc1]

A flask was flushed with nitrogen and charged with tris(dibenzylidenacetone)dipalladium(0) (211 mg, 0.23 mmol), tri-tert-butylphosphine (186 mg, 0.92 mmol) and deaerated o-xylene (30 mL). After stirring for 30 min under a nitrogen atmosphere at ambient temperature, 7-(4-bromophenyl)dibenzo[c,h]acridine (10 g, 23 mmol), 3,6-diphenyl-9H-carbazole (8.8 g, 27.6 mmol), $K_2CO_3$ (9.5 g, 69 mmol), 18-crown-6 (1.2 g, 0.46 mmol), and additional deaerated o-xylene (200 mL) were added. The resulting reaction mixture was heated to reflux under a nitrogen atmosphere for 48 h. After cooling down to 10° C., the formed precipitate was collected by suction filtration and washed with n-hexane. The obtained solid was dissolved in chloroform and extracted with water five times. After drying over $MgSO_4$, the organic phase was filtered, concentrated under reduced pressure and n-hexane was added. The obtained precipitate was collected by suction filtration and washed with n-hexane. Further purification was achieved by recrystallization from toluene. After drying, 11.7 g (76%) of a pale yellow solid were obtained. Final purification was achieved by sublimation. HPLC/ESI-MS: 99.6%, m/z=673 ([M+H]$^+$).

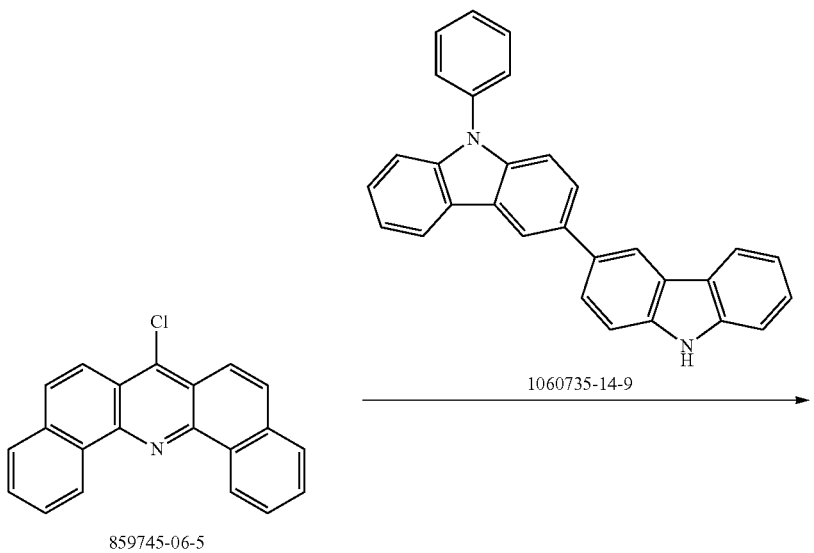

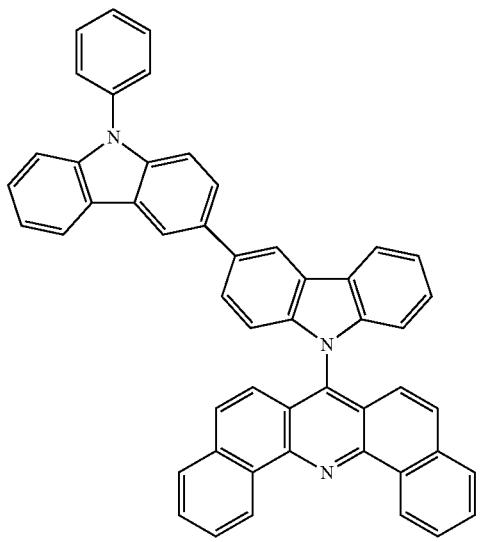 [SMILES: c1ccc(-n2c3ccccc3c3cc(-c4ccc5c(c4)c4ccccc4n5-c4c5ccc6ccccc6c5nc5c4ccc4ccccc45)ccc32)cc1]

7-(9'-phenyl-9H,9'H-[3,3'-bicarbazol]-9-yl)dibenzo[c,h]acridine (Compound 6)

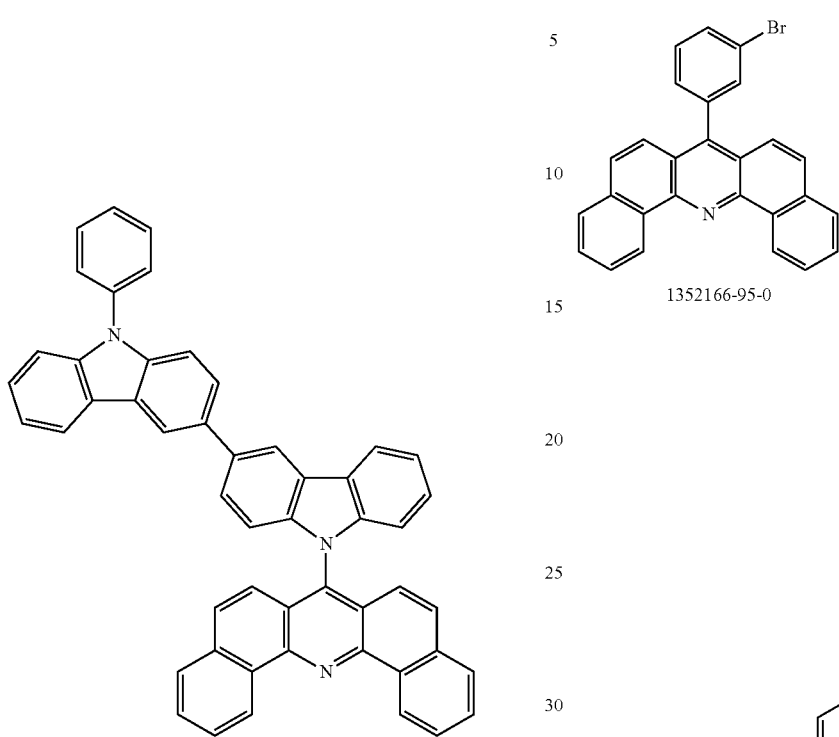

A flask was flushed with nitrogen and charged with sodium hydride (616 mg, 25.7 mmol) and anhydrous dimethylformamide (135 mL). The suspension was stirred at 0° C. for 30 minutes. Then 9-phenyl-9H,9'H-3,3'-bicarbazole (10.0 g, 24.5 mmol) was added portionwise and the reaction mixture was stirred at room temperature for 90 minutes. 7-chlorodibenzo[c,h]acridine (8.5 g, 26.9 mmol) was added and the reaction mixture was stirred at 110° C. for 4 hours. The reaction was quenched with methanol (100 mL) and the precipitate formed was filtered and washed with methanol. The obtained solid was dissolved in chloroform/toluene 1/1 (500 mL) and filtered through a pad of silica gel. After rinsing with additional chloroform/toluene 1/1, the filtrate was concentrated under reduced pressure and the suspension was stirred at room temperature overnight. The obtained precipitate was collected by suction filtration and washed with toluene. The crude solid was dissolved in hot THF, ethanol was slowly added and the suspension was stirred overnight at room temperature. The precipitate was collected by suction filtration and further purified by column chromatography (eluting with dichloromethane/hexane 1/3 to pure dichloromethane at the end). The solid was dissolved in hot THF, ethanol was slowly added and the suspension was stirred overnight at room temperature, then solid was filtered. After drying, 8.8 g (52%) of a solid were obtained. Final purification was achieved by sublimation. HPLC/ESI-MS: 100%, m/z=686 ([M+H]$^+$).

N-(3-(dibenzo[c,h]acridin-7-yl)phenyl)-N-phenylnaphthalen-2-amine (Compound 7)

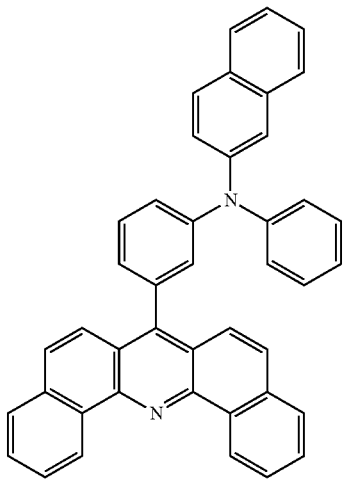 [SMILES: c1ccc(N(c2cccc(-c3c4ccc5ccccc5c4nc4c3ccc3ccccc34)c2)c2ccc3ccccc3c2)cc1]

A flask was flushed with nitrogen and charged with 7-(3-bromophenyl)dibenzo[c,h]acridine (10.0 g, 23.0 mmol), N-phenylnaphthalen-2-amine (5.6 g, 25.33 mmol), KO$^t$Bu (7.75 g, 69.1 mmol), Bis(dibenzylideneaceton)palladium (278 mg, 0.46 mmol), tri-tert-butylphosphine (140 mg, 0.69 mmol) and deaerated toluene (230 mL). The resulting reaction mixture was heated to 80° C. under a nitrogen atmosphere for 5 hours. After cooling down to room temperature, the formed precipitate was collected by suction filtration and washed with toluene. The obtained solid was stirred in water for 30 minutes at room temperature, then it was filtered, washed with water and dried. Crude solid was dissolved in toluene and filtered through a pad of silica gel. After rinsing with additional toluene, the filtrate was concentrated under reduced pressure and the suspension was stirred at room temperature overnight. The obtained precipitate was collected by suction filtration and washed with n-hexane. Further purification was achieved by recrystallization from acetone. Finally, the solid was dissolved in hot toluene, n-hexane was slowly added and the suspension was stirred overnight at room temperature, then solid was filtered. After drying, 8.5 g (64%) of a solid were obtained. Final purification was achieved by sublimation. HPLC/ESI-MS: 100%, m/z=573 ([M+H]$^+$).

Procedure for Fabrication of OLEDs

For top emission OLED devices types A and B (top emission devices) a glass substrate with dimensions of 150 mm×150 mm×0.7 mm was ultrasonically cleaned with a 2% aquatic solution of Deconex FPD 211 for 7 minutes and then with pure water for 5 minutes, and dried for 15 minutes in a spin rinse dryer. Subsequently, 100 nm Ag were deposited as anode at a pressure of 10-5 to 10-7 mbar. For bottom emission OLED device, OLED device type C, a UV-Ozone cleaned ITO/glass substrate was used instead of a glass substrate.

Then, HT-1 and D-1 were vacuum co-deposited at a wt % ratio of 92:8 on the anode to form a HIL. Then, HT-1 was vacuum deposited on the HIL, to form an HTL. Then, HT-2 was vacuum deposited on the HTL to form an electron blocking layer (EBL).

Afterwards the emission layer was formed on the EBL by co-deposition of HOST-1 and EMITTER-1 in the wt % ratio of 97:3.

Then, for top emission OLED devices type A, ET-1 was vacuum deposited onto the emission layer to form the hole blocking layer (HBL). Then, the electron transporting layer is formed on the hole blocking layer by co-deposition of the compounds of Formula (I), or the comparative compound-1, and lithium quinolate (LiQ) in a wt % ratio of 1:1.

For top emission OLED devices type B, the compounds of Formula (I) were vacuum deposited onto the emission layer to form the hole blocking layer. Then, the electron transporting layer is formed on the hole blocking layer by co-deposition ET-2 and lithium quinolate (LiQ) in a wt % ratio of 1:1.

Then, for both top emission OLED devices of type A and B the electron injection layer is formed on the electron transporting layer by deposing Yb.

Ag is evaporated at a rate of 0.01 to 1 Å/s at 10-7 mbar to form a cathode.

A cap layer of N-([1,1'-biphenyl]-4-yl)-9,9-dimethyl-N-(4-(9-phenyl-9H-carbazol-3-yl)phenyl)-9H-fluoren-2-amine is formed on the cathode.

For bottom emission OLED device, OLED device type C, HT-1 and D-1 were vacuum co-deposited at a wt % ratio of 97:3 on the ITO to form a HIL. Then, HT-1 was vacuum deposited on the HIL to form an HTL. Then, HT-3 was vacuum deposited on the HTL form an electron blocking layer (EBL).

Afterwards the emission layer was deposited by co-deposition of HOST-2:compound of Formula (I):EMITTER-2 in a wt % ratio of 49:49:2 and the emission layer.

Afterwards, ET-1 was vacuum deposited onto the emission layer to form the hole blocking layer. Then, the electron transporting layer is formed on the hole blocking layer by co-deposition ET-2 and lithium quinolate (LiQ) in a wt % ratio of 1:1.

Then, the electron injection layer is formed on the electron transporting layer by depositing LiQ.

Then, Ag is evaporated at a rate of 0.01 to 1 Å/s at 10-7 mbar to form a cathode.

Examples

Table 1: Performance of an organic electroluminescent device comprising an a compound of formula 1 in the emission layer ETL, in the auxiliary ETL or in the EML.

OLED devices of 3 types (A, B and C) were prepared in order to test the inventive compounds of Formula (I). The details of the layer stack in the OLED devices are given below. A slash "/" separates individual layers. Layer thicknesses are given in squared brackets [ . . . ], mixing ratios in wt % given in round brackets ( . . . ):

OLED device type A: The compound of Formula (I) or the comparative compound is comprised in the electron transport layer. Layer stack: silver [100 nm]/HT-1:D-1 (92:8) [10 nm]/HT-1 [118 nm]/HT-2 [5 nm]/HOST-1:EMITTER-1 (97:3) [20 nm]/ET-1 [5 nm]/compound of Formula (I):LiQ or the comparative compound:LiQ (1:1) [31 nm]/Yb [2 nm]/silver [11 nm]

OLED device type B: The compound of Formula (I) is comprised in the hole blocking layer. Layer stack: silver [100 nm]/HT-1:D-1 (92:8) [10 nm]/HT-1 [125 nm]/HT-2 [5 nm]/HOST-1:EMITTER-1 (97:3) [20 nm]/compound of Formula (I) [5 nm]/ET-2:LiQ (1:1) [31 nm]/Yb [2 nm]/silver [11 nm]

OLED device type C: The compound of Formula (I) is comprised in the emission layer. Layer stack: ITO/HT-1:D-1 (97:3) [10 nm]/HT-1 [144 nm]/HT-3 [70 nm]/HOST-2:compound of Formula (I):EMITTER-2 (49:49:2) [40 nm]/ET-1 [5 nm]/ET-2:LiQ (1:1) [31 nm]/LiQ [2 nm]/silver [100 nm]

Technical Effect of the Invention

In Table 1 below, material properties of compounds of Formula (I) and the comparative compounds are shown.

In Table 2 below, dipole moment, HOMO energy level and LUMO energy level and the energy gap LUMO—HOMO of compounds of Formula (I) are shown. Compounds of Formula (I) have an energy gap LUMO—HOMO which is lower than 3.89 eV.

In Table 3 below operating voltage and lifetime LT97 at 30 mA/cm2 (h) are shown of an OLED comprising a compound of Formula (I).

It is evident from Table 3, that the operating lifetime LT97 at 30 mA/cm2 (h) is improved for all examples 1 to 9 compared to comparative examples by at least 28% or more. Without being bound by theory, the improvement in LT may be due to reduced degradation of the compound of Formula (I) during fabrication of the OLED.

List of Compounds Used

| | IUPAC name | Reference |
|---|---|---|
| HT-1 | Biphenyl-4-yl(9,9-diphenyl-9H-fluoren-2-yl)-[4-(9-phenyl-9H-carbazol-3-yl)phenyl]-amine (CAS 1242056-42-3) | US2016322581 |

-continued

|  | IUPAC name | Reference |
|---|---|---|
| HT-2 | N,N-bis(4-(dibenzo[b,d]furan-4-yl)phenyl)-[1,1':4',1''-terphenyl]-4-amine (CAS 1198399-61-9) | JP2014096418 |
| HT-3 | N,N-di([1,1'-biphenyl]-4-yl)-7,7-dimethyl-7H-fluoreno[4,3-b]benzofuran-10-amine (CAS 1616706-52-5) | US2015280136 |
| D-1 | 4,4',4''-((1E,1'E,1''E)-cyclopropane-1,2,3-triylidenetris(cyanomethanylylidene))tris(2,3,5,6-tetrafluorobenzonitrile) | US2008265216 |
| HOST-1 | H09 (Fluorescent-blue host material) | Commercially available from Sun Fine Chemicals, Inc, S. Korea |
| HOST-2 | 5,8-di([1,1'-biphenyl]-4-yl)-5,8-dihydroindolo[2,3-c]carbazole (CAS 222044-79-3) |  |
| EMITTER-1 | BD200 (Fluorescent-blue emitter material) | Commercially available from Sun Fine Chemicals, Inc, S. Korea |
| EMITTER-2 | Bis(2-(3,5-dimethylphenyl)quinolinato)(acetylacetonate)iridium(III) (CAS 1056874-46-4) |  |
| ET-1 | 2,4-diphenyl-6-(4',5',6'-triphenyl-[1,1':2',1'':3'',1''':3''',1''''-quinquephenyl]-3''''-yl)-1,3,5-triazine (CAS 2032364-64-8) | WO2016171358 |
| ET-2 | 2-([1,1'-biphenyl]-4-yl)-4-(9,9-diphenyl-9H-fluoren-4-yl)-6-phenyl-1,3,5-triazine (CAS 1801992-44-8) | KR101537500 |
| LiQ | 8-Hydroxyquinolinolato-lithium (CAS 850918-68-2) | WO2013079217 |

TABLE 1

Properties of compounds of Formula (I) and comparative compounds.

|  | Structure | mp (° C.) | Tg (° C.) | $T_{RO}$ (° C.) |
|---|---|---|---|---|
| Comparative-1 reference: EP3312899 A1 | 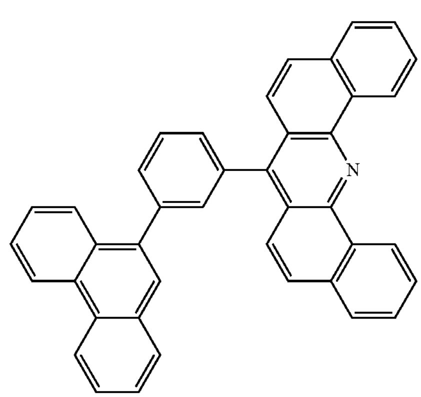 [SMILES: c1cc(-c2cc3ccccc3c3ccccc23)cc(-c2c3ccc4ccccc4c3nc3c2ccc2ccccc23)c1] | 251 | 123 | 218 |

TABLE 1-continued

Properties of compounds of Formula (I) and comparative compounds.

| Structure | mp (°C.) | Tg (°C.) | $T_{RO}$ (°C.) |
|---|---|---|---|
| Comparative-2 reference: WO2016180891 | 329 | 144 | 272 |
| Compound 1 | 336 | 127 | 245 |
| Compound 2 | 277 | 119 | 214 |

TABLE 1-continued

Properties of compounds of Formula (I) and comparative compounds.

| Structure | mp (° C.) | Tg (° C.) | $T_{RO}$ (° C.) |
|---|---|---|---|
| Compound 3 | 312 | 156 | 288 |
| Compound 4 | 308 | 139 | 291 |
| Compound 5 | 281 | 141 | 238 |

TABLE 1-continued

Properties of compounds of Formula (I) and comparative compounds.

| | Structure | mp (° C.) | Tg (° C.) | T$_{RO}$ (° C.) |
|---|---|---|---|---|
| Compound 6 | 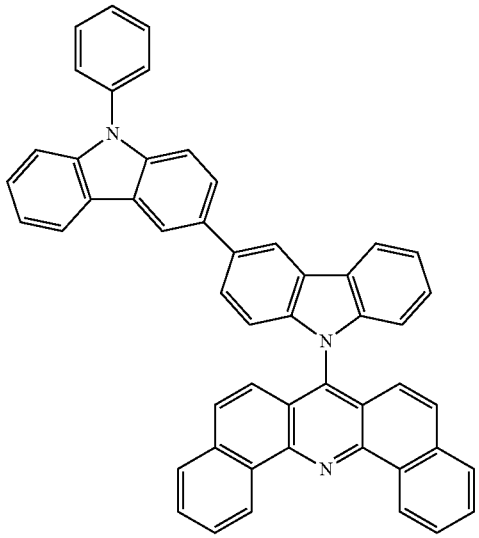 [SMILES: c1ccc(-n2c3ccccc3c3cc(-c4ccc5c(c4)c4ccccc4n5-c4c5ccc6ccccc6c5nc5c4ccc4ccccc45)ccc32)cc1] | — | 181 | 280 |
| Compound 7 | 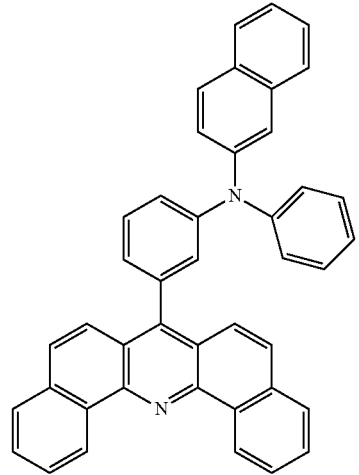 [SMILES: c1ccc(N(c2cccc(-c3c4ccc5ccccc5c4nc4c3ccc3ccccc34)c2)c2ccc3ccccc3c2)cc1] | 264 | 113 | 216 |

TABLE 2

Dipole moment, HOMO and LUMO energy levels, Energy gap LUMO − HOMO of compounds of Formula (I) and comparative compounds, simulated by DFT (B3LYP_Gaussian/6-31G*, gas phase)

| | Dipole moment [Debye] | HOMO [eV] | LUMO [eV] | Energy gap LUMO − HOMO [eV] |
|---|---|---|---|---|
| Comparative-1 | 1.89 | −5.63 | −1.74 | 3.89 |
| Comparative-2 | 2.59 | −5.67 | −1.78 | 3.89 |
| Compound 1 | 0.05 | −5.43 | −1.84 | 3.59 |
| Compound 2 | 1.40 | −5.42 | −1.83 | 3.59 |
| Compound 3 | 1.63 | −5.26 | −1.84 | 3.42 |
| Compound 4 | 0.40 | −5.28 | −1.86 | 3.42 |
| Compound 5 | 6.88 | −5.84 | −1.97 | 3.87 |
| Compound 6 | 1.30 | −5.04 | −1.99 | 3.05 |
| Compound 7 | 2.08 | −5.05 | −1.71 | 3.34 |

TABLE 3

OLED devices comprising compounds of formula 1 and comparative compounds.

| OLED device example name | OLED device type | Compounds in layer comprising a compound of Formula (I) | Ratio of compounds in layer comprising compound of Formula (I) | Operating voltage at 10 mA/cm² (V) | LT97 at 30 mA/cm² (h) |
|---|---|---|---|---|---|
| Comparative example 1 | A | Comparative-1:LiQ | 1:1 | 3.51 | 32 |
| Comparative example 2 | A | Comparative-2:LiQ | 1:1 | 3.61 | 30 |
| Example-1 | A | Compound 1:LiQ | 1:1 | 3.47 | 41 |
| Example-2 | A | Compound 2:LiQ | 1:1 | 3.62 | 43 |
| Example-3 | A | Compound 3:LiQ | 1:1 | 3.71 | 49 |
| Example-4 | A | Compound 4:LiQ | 1:1 | 3.66 | 50 |
| Example-5 | A | Compound 5:LiQ | 1:1 | 3.98 | 101 |
| Example-6 | A | Compound 6:LiQ | 1:1 | 3.48 | 42 |
| Example-7 | B | Compound 3 | 1 | 3.69 | 73 |
| Example-8 | B | Compound 4 | 1 | 3.72 | 97 |
| Example-9 | C | Compound 6:HOST-2:EMITTER-2 | 49:49:2 | 3.69 | 63 |

The features disclosed in the foregoing description and in the dependent claims may, both separately and in any combination thereof, be material for realizing the aspects of the disclosure made in the independent claims, in diverse forms thereof.

The invention claimed is:

1. Compound of the Formula (I)

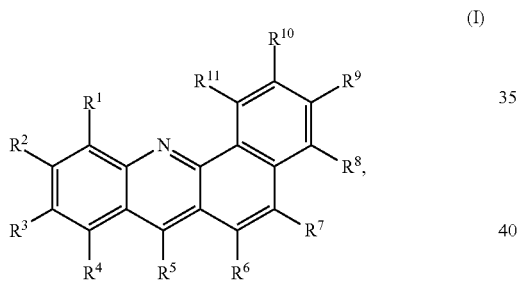

wherein all of $R^1$ to $R^{11}$, except one, are independently selected from the group consisting of H, D, F, substituted or unsubstituted $C_1$ to $C_{18}$ alkyl, substituted or unsubstituted $C_6$ to $C_{42}$ aryl, substituted or unsubstituted $C_3$ to $C_{42}$ heteroaryl; and adjacent groups $R^1$ to $R^{11}$ may be linked to each other to form a fused ring, wherein the one of $R^1$ to $R^{11}$ not selected from the above groups is a group G, wherein
the group G comprises one atom A having an electron pair in a p-orbital thereof;
the group G comprises two 6-membered aryl rings which are attached to the atom A, wherein each of the two 6-membered aryl rings is attached to the atom A via a single bond respectively; and wherein the two 6-membered aryl rings attached to the atom A may be connected with each other via a single bond;
the group G comprises 12 to 66 carbon atoms in total;
the group G is attached to the benzoacridine part of the compound of formula (I) via a single bond or via a $C_6$ to $C_{18}$ arylene group, wherein the $C_6$ to $C_{18}$ arylene group is part of the group G; and
the group G is unsubstituted or substituted with one or more substituents independently selected from the group consisting of D, F, $C_1$ to $C_{18}$ alkyl, $C_6$ to $C_{42}$ aryl, $C_6$ to $C_{42}$ heteroaryl, $(R^{12})_2P$=O, CN or G',
wherein the group G' is defined likewise group G with the exception that the group G' is not attached to the benzoacridine part of the compound of formula (I) but to the group G via a single bond or via a $C_6$ to $C_{18}$ arylene group, wherein the $C_6$ to $C_{18}$ arylene group is part of the group G' provided that in case that the group G is attached to the benzoacridine part of the compound of formula (I) via the $C_6$ to $C_{18}$ arylene group, substituents which may be attached to the $C_6$ to $C_{18}$ arylene group are only selected from the group consisting of $C_1$ to $C_{18}$ alkyl, $C_6$ to $C_{42}$ aryl, $(R^{12})_2P$=O and CN;
wherein in case that at least one of $R^1$ to $R^{11}$, which is not the group G, is substituted, the respective substituent or substituents are independently selected from the group consisting of D, F, $C_1$ to $C_{18}$ alkyl, $C_6$ to $C_{36}$ aryl, $C_6$ to $C_{42}$ heteroaryl, $(R^{12})_2P$=O, CN; and
wherein $R^{12}$ are independently selected from the group consisting of $C_1$ to $C_{18}$ alkyl and $C_6$ to $C_{24}$ aryl;
wherein the group G comprises the following structural element

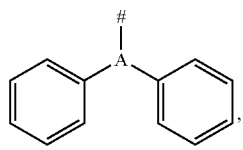

wherein
the group G is attached to the benzoacridine part of the compound of Formula (I) at the position indicated by "#", wherein
the two 6-membered aryl rings may be linked with each other via a single bond.

2. Compound according to claim 1, wherein the group G comprises 1 to 5 heteroatoms selected from the group consisting of N, S and O.

3. Compound according to claim 1, wherein the atom A is.

4. Compound according to claim 1, wherein the total number of aromatic rings comprised in the compound of Formula (I) is from 6 to 21.

5. Compound according to claim 1, wherein $R^1$ and $R^2$; or $R^2$ and $R^3$; or $R^3$ and $R^4$; are linked to form an aryl ring structure.

6. Compound according to claim 1, wherein $R^5$ or $R^{10}$ is the group G.

7. Organic electronic device comprising an organic semiconducting layer, wherein the organic semiconducting layer comprises the compound of the Formula (I) according to claim 1.

8. Organic electronic device according to claim 7 further comprising a first electrode and a second electrode, wherein the organic semiconducting layer is arranged between the first electrode and the second electrode.

9. Organic electronic device according to claim 7, wherein the organic semiconducting layer is an emission layer.

10. Organic electronic device according to claim 7, wherein the organic semiconducting layer is a hole blocking layer.

11. Organic electronic device according to claim 7, wherein the organic semiconducting layer is an electron transport layer.

12. Organic electronic device according to claim 7, wherein the organic semiconducting layer further comprises at least one second compound which is not a compound of formula (I).

13. Display device comprising the organic electronic device according to claim 7.

14. Lighting device comprising the organic electronic device according to claim 7.

* * * * *